US012678529B2

(12) United States Patent
Losser

(10) Patent No.: US 12,678,529 B2
(45) Date of Patent: Jul. 14, 2026

(54) UV AIR PURIFIER WITH BAFFLE SYSTEM

(71) Applicant: FELLOWES, INC., Itasca, IL (US)

(72) Inventor: James Losser, St. Charles, IL (US)

(73) Assignee: FELLOWES, INC., Itasca, IL (US)

( * ) Notice: Subject to any disclaimer, the term of this patent is extended or adjusted under 35 U.S.C. 154(b) by 442 days.

(21) Appl. No.: 18/372,258

(22) Filed: Sep. 25, 2023

(65) Prior Publication Data

US 2024/0157016 A1 May 16, 2024

Related U.S. Application Data

(60) Provisional application No. 63/411,909, filed on Sep. 30, 2022.

(51) Int. Cl.
B01D 53/22 (2006.01)
A61L 9/20 (2006.01)
(Continued)

(52) U.S. Cl.
CPC ............ A61L 9/20 (2013.01); B01D 46/0028 (2013.01); B01D 46/0049 (2013.01);
(Continued)

(58) Field of Classification Search
CPC .... A61L 9/20; A61L 2209/12; A61L 2209/14; F24F 8/22; F24F 8/108; F24F 13/08;
(Continued)

(56) References Cited

U.S. PATENT DOCUMENTS

| | | | |
|---|---|---|---|
| 2,359,021 A | | 9/1944 | Campbell et al. |
| 2,824,343 A | * | 2/1958 | Glass ........................ A61L 9/20 |
| | | | D23/366 |

(Continued)

FOREIGN PATENT DOCUMENTS

| | | |
|---|---|---|
| CN | 107496969 A | 12/2017 |
| DE | 10-2021-104060 A1 | 8/2022 |

(Continued)

OTHER PUBLICATIONS

International Search Report and Written Opinion issued in corresponding International Application No. PCT/US2023/033639, dated Jun. 18, 2024.
(Continued)

*Primary Examiner* — Anthony Shumate
(74) *Attorney, Agent, or Firm* — CUSHMAN PARTNERS, LLC

(57) ABSTRACT

One aspect of the invention provides an air purifier with a plurality of baffles mounted adjacent a first port. The baffles are arranged in a spaced apart arrangement to provide a series of flow channels. Port guiding surfaces direct the air flowing between the flow channels and the first port and chamber guiding surfaces direct the air flowing between the flow channels and the sterilizing chamber. Another aspect of the invention provides an air purifier with a plurality of baffles mounted adjacent a second port for receiving the air flow out from the fan into the sterilizing chamber. The baffles provide a series of port guiding surfaces for directing the air flowing from the fan generating the flow through the second port, and a series of chamber guiding surfaces oriented generally in the flow direction for directing air flowing from the baffles into the sterilizing chamber.

39 Claims, 13 Drawing Sheets

(51) Int. Cl.

| | |
|---|---|
| *B01D 46/00* | (2022.01) |
| *F24F 8/108* | (2021.01) |
| *F24F 8/22* | (2021.01) |
| *F24F 13/08* | (2006.01) |

(52) U.S. Cl.
CPC .............. *F24F 8/108* (2021.01); *F24F 8/22* (2021.01); *F24F 13/08* (2013.01); *A61L 2209/12* (2013.01); *A61L 2209/14* (2013.01); *B01D 2273/30* (2013.01); *B01D 2279/65* (2013.01)

(58) Field of Classification Search
CPC ............ B01D 46/0028; B01D 46/0049; B01D 2273/30; B01D 2279/65
See application file for complete search history.

(56) References Cited

U.S. PATENT DOCUMENTS

| | | | |
|---|---|---|---|
| 4,730,551 | A | 3/1988 | Peludat |
| 5,352,359 | A * | 10/1994 | Nagai ..................... C02F 1/325 210/748.11 |
| 5,505,904 | A | 4/1996 | Haidinger et al. |
| 5,601,786 | A | 2/1997 | Monagan |
| 6,053,968 | A | 4/2000 | Miller |
| 6,290,266 | B1 | 9/2001 | Kawano |
| 6,328,937 | B1 | 12/2001 | Glazman |
| 6,497,840 | B1 | 12/2002 | Palestro et al. |
| 8,350,228 | B2 | 1/2013 | Welker |
| 8,439,517 | B2 | 5/2013 | Welker |
| 9,457,120 | B2 | 10/2016 | Matsui |
| 9,517,280 | B2 | 12/2016 | Lynn et al. |
| 9,522,210 | B2 | 12/2016 | Worrilow |
| 9,737,842 | B2 | 8/2017 | Matlin et al. |
| 11,028,223 | B2 | 6/2021 | Niemiec et al. |
| 11,105,522 | B2 | 8/2021 | Kleinberger et al. |
| 11,202,847 | B1 | 12/2021 | Lan et al. |
| 11,219,701 | B1 * | 1/2022 | Sahu .......................... A61L 9/20 |
| 2002/0031460 | A1 | 3/2002 | Kulp |
| 2003/0217641 | A1 | 11/2003 | Palestro |
| 2005/0069465 | A1 * | 3/2005 | McEllen .................. A61L 9/015 422/4 |
| 2005/0191205 | A1 | 9/2005 | Uslenghi |
| 2007/0114442 | A1 * | 5/2007 | Chen ....................... C02F 1/325 250/455.11 |
| 2009/0200155 | A1 * | 8/2009 | Cuffaro ..................... A61L 9/20 15/353 |
| 2011/0318237 | A1 * | 12/2011 | Woodling ............... C02F 1/325 422/186.3 |
| 2016/0303271 | A1 | 10/2016 | Livchak |
| 2020/0122078 | A1 * | 4/2020 | Trent ................. B01D 53/8668 |
| 2020/0363685 | A1 * | 11/2020 | He ......................... G02F 1/1303 |
| 2021/0003310 | A1 | 1/2021 | Shnaiderman et al. |
| 2022/0234002 | A1 * | 7/2022 | Trent .................... B01D 53/75 |

| | | | |
|---|---|---|---|
| 2022/0313847 | A1 * | 10/2022 | Fulbrook .................. A61L 2/10 |
| 2023/0158197 | A1 * | 5/2023 | Godbout .............. B01D 46/521 96/224 |
| 2025/0090715 | A1 * | 3/2025 | Greene ..................... A61L 9/20 |

FOREIGN PATENT DOCUMENTS

| | | | |
|---|---|---|---|
| EP | 3967941 | A1 | 3/2022 |
| GB | 2468504 | A | 9/2010 |
| GB | 2515842 | A | 1/2015 |
| KR | 20-0374471 | Y1 | 1/2005 |
| KR | 10-0503258 | B1 | 7/2005 |
| KR | 10-0564907 | B1 | 3/2006 |
| KR | 10-2007-0047105 | A | 5/2007 |
| KR | 20-0437892 | Y1 | 1/2008 |
| KR | 10-2008-0069556 | A | 7/2008 |
| KR | 10-2008-0073472 | A1 | 8/2008 |
| KR | 20-2010-0006034 | U | 6/2010 |
| KR | 10-2010-0119627 | A | 11/2010 |
| KR | 20-2017-0003584 | U | 10/2017 |
| KR | 10-2160608 | B1 | 9/2020 |
| WO | 2012/068569 | A1 | 5/2012 |
| WO | 2022/027101 | A1 | 2/2022 |

OTHER PUBLICATIONS

Gwangpyo Ko et al., "The Characterization of Upper-Room Ultraviolet Germicidal Irradiation in Inactivating Airborne Microorganisms," Environmental Health Perspectives, vol. 110, No. 1 (Jan. 2002). on the Performance of the VidaShield System, http://vidashield.com/files/(2011).

Wladyslaw J. Kowalski, "Report on the Performance of the VidaShield System," http://vidashield.com/files/whitepaper/dr-kowalski-vidashield-final-report.pdf (2011).

Sanitaire Room Air Sanitizer Model RSCS280, Installation, Operation & Maintenance Owner's Manual, Manufacturer Atlantic Ultraviolet Corporation, Document No. 98-1133C (Rev. Jan. 2011).

Vidashield Installation and Operating Instructions for Continuous Antimicrobial Air Cleaner, Manufacturer American Green Technology, https://vidashield.com/files/vs-installation-operation.pdf (Rev. May 31, 2016).

Vidashield Fast, Continuous UV-C Air Purification System trifold.

Dr. Wladyslaw J. Kowalsky, "Report on the Performance of the Vidashield UV24 Air Purification System," prepared for Medical Illumination International, Inc., (Dec. 7, 2011). https://www.armstrongceilings.com/content/dam/armstrongceilings/commercial/north-america/whitepapers/performance-report-vidashield-uv24-air-purification-system.pdf.

International Search Report and Written Opinion issued in corresponding International Patent Application No. PCT/US2023/033639 dated Dec. 22, 2023.

International Preliminary Report on Patentability issued in corresponding International Patent Application No. PCT/US2023/033639 dated Dec. 16, 2024.

* cited by examiner

L-Stack
(Fan side)

L-stack
(UV port side)

UV AIR PURIFIER WITH BAFFLE SYSTEM

RELATED APPLICATION(S)

The present application claims priority to U.S. Provisional Application Ser. No. 63/411,909, filed Sep. 30, 2022, the entirety of which is incorporated herein.

FIELD OF THE INVENTION

The present invention relates to an air purifier using ultraviolet (UV) light for sterilizing the air.

BACKGROUND OF THE INVENTION

Air purifiers using light radiating in the UV spectrum, often in the UV-C spectrum, have been used for purifying air. UV light is known for its ability to eliminate pathogens, such as bacteria and viruses, in the air flowing through a purifier. The principle of operation is believed to be the ability of UV light to disrupt the DNA of the pathogen, thus effectively killing the pathogen.

One issue of concern with air purifiers using UV light is leakage. Leakage is the escape of the light from the interior of the air purifier into the room in which it is located. In a stand-alone air purifier, i.e., a purifier not designed to be mounted in or to a wall or ceiling, there is more freedom to use covers, shields, and the like because such devices are less subject to space as a design constraint. U.S. Pat. No. 6,053,968 discloses such a design, in which the air purifier is portable and can be located anywhere withing a room.

However, for devices that are designed to be installed in or to a wall or ceiling, generally such devices are designed to be thinner in the direction perpendicular to the wall or ceiling, thus making them more compact with a low-profile and easier to fit inside a wall or ceiling, or be less obtrusive when mounted in a wall or ceiling. Often, the inlet and outlet ports for such purifiers have grills or screens, but grills/ screens are not sufficient to prevent UV light leakage from the air purifier. U.S. Pat. No. 11,202,847 discloses a UV sterilizing air purifier for ceiling installation that purportedly slows down the air flow over a transversely mounted bulb. That design has the problem that its ability to achieve higher volumetric flow by increasing flow rate is constrained by the need for adequate exposure time to the UV radiation. It also has the shortcoming that its design has no adequate means for addressing the leakage of UV radiation. For example, FIG. 5 of that patent shows a space under the fan that leads to its associated grill, through which UV radiation can readily leak.

Armstrong markets an air purifier under the brand VidaShield, which uses a singular restricted tortuous or undulating path between the inlet/outlet grill and the sterilizing chamber where the UV light is emitted. The VidaShield has anti-reflective coating within the tortuous or undulating path, but the light leakage is also managed by the length of the path as well as its restriction, which reduces the overall volumetric flow rate.

The inventors have recognized that a competing demand with blocking leakage of UV light is the ability to manage the airflow to ensure increased exposure of the air being purified to the UV light without significant impact on the volumetric flow rate for turnover of the air in the room/space being cleaned.

SUMMARY OF THE INVENTION

One aspect of the present application provides an air purifier comprising a housing for installation in or on a wall or ceiling of a building space; a UV light sterilizing chamber in the housing for directing a flow of air therethrough in a flow direction extending between first and second opposing ends of the chamber; a UV light source mounted in the sterilizing chamber for emitting UV light to sterilize air flowing through the sterilizing chamber; and a first port on the housing communicated to the UV light sterilizing chamber at the first end thereof for permitting flow of the air between the sterilizing chamber and the building space via the first port. The first port is oriented at an angle to the flow direction for facing the building space. A fan generates the flow of the air from the building space and through the UV light sterilizing chamber and first port. The fan is distal from the first port. A plurality of baffles is mounted adjacent the first port. The plurality of baffles are arranged in a spaced apart arrangement to provide a series of flow channels including a series of port guiding surfaces and a series of chamber guiding surfaces. The port guiding surfaces are configured to direct the air flowing between the flow channels and the first port and the chamber guiding surfaces are configured to direct the air flowing between the flow channels and the sterilizing chamber.

In an embodiment, the baffles of the plurality thereof may have anti-reflective surfaces that reduce or eliminate reflection of the UV light emitted by the UV light source to reduce or eliminate emittance through the first port.

In some embodiments, the port guiding surfaces may be oriented towards the first port for directing the air flowing between the flow channels and the first port, and the chamber guiding surfaces may be oriented towards the sterilizing chamber generally in the flow direction for directing air flowing between the flow channels and the sterilizing chamber. In other embodiments, the chamber guiding surfaces for directing the air flowing between the flow channels and the sterilizing chamber may be oriented generally perpendicularly to the flow direction, and they may be essentially perpendicular or perpendicular.

Another aspect of the present application provides an air purifier comprising a housing for installation in or on a wall or ceiling of a building space; a UV light sterilizing chamber in the housing for directing a flow of air therethrough in a flow direction extending between first and second opposing ends of the chamber; a UV light source mounted in the sterilizing chamber for emitting UV light to sterilize air flowing through the sterilizing chamber; a first port on the housing communicated to the UV light sterilizing chamber at the first end thereof for permitting flow of the air between the sterilizing chamber and the building space via the first port; and a second port on the housing communicated to the UV light sterilizing chamber at the second end thereof for permitting flow of the air between the sterilizing chamber and the building space via the second port. A fan adjacent the second port generates the flow of the air to draw the flow of air in from the building space through the second port and deliver the flow of air through the UV light sterilizing chamber and out the first port. A plurality of baffles is mounted adjacent the second port and the fan for receiving the air flowing out from the fan into the sterilizing chamber. The baffles of the plurality provides a series of port guiding surfaces for directing the air flowing from the fan generating the flow through the second port. The baffles of the plurality also provide a series of chamber guiding surfaces oriented generally in the flow direction for directing air flowing from the baffles into the sterilizing chamber.

Other objects, features and advantages of the present invention will become apparent from the following detailed description, the accompanying drawings, and the appended claims.

DETAILED DESCRIPTION OF THE ILLUSTRATED EMBODIMENT(S)

Figure 1:
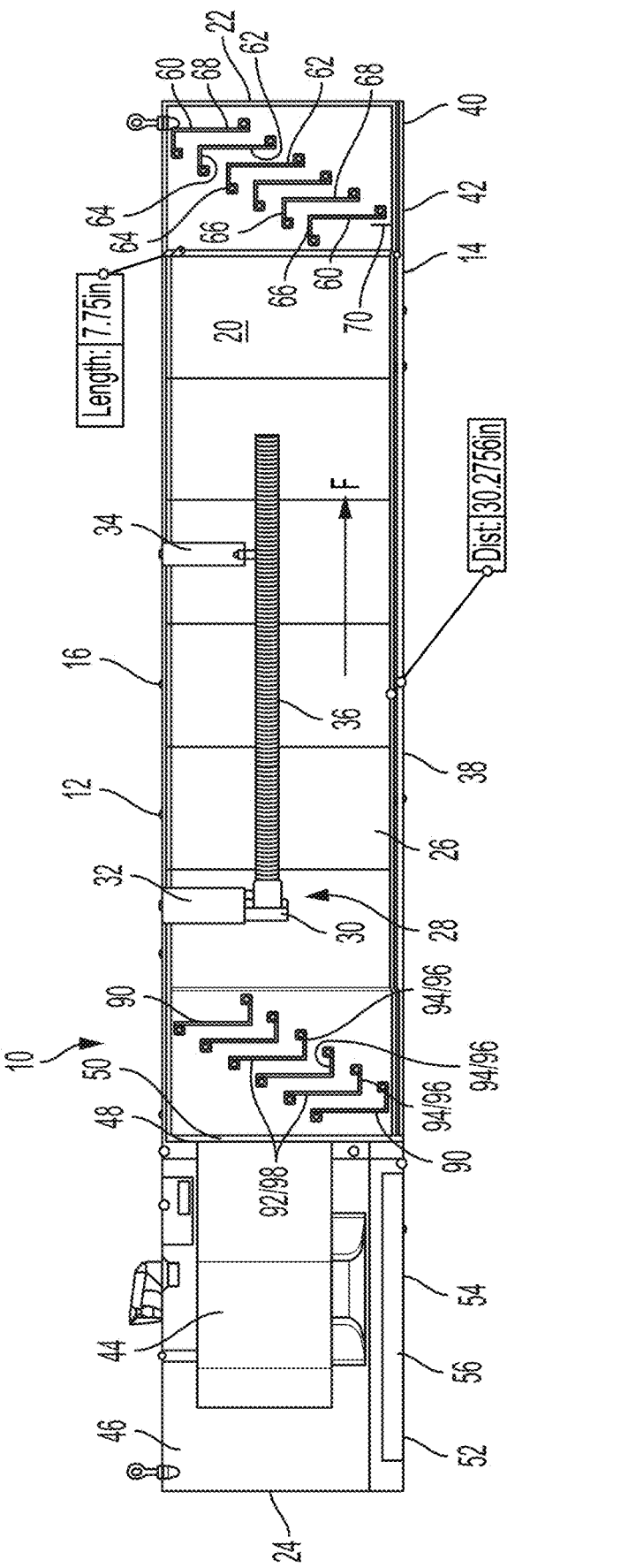
FIG. 1 is a schematic longitudinal cross-section view of an air purifier according to an embodiment of the present application with the side wall removed to illustrate the basic structures thereof.
Figure 2:
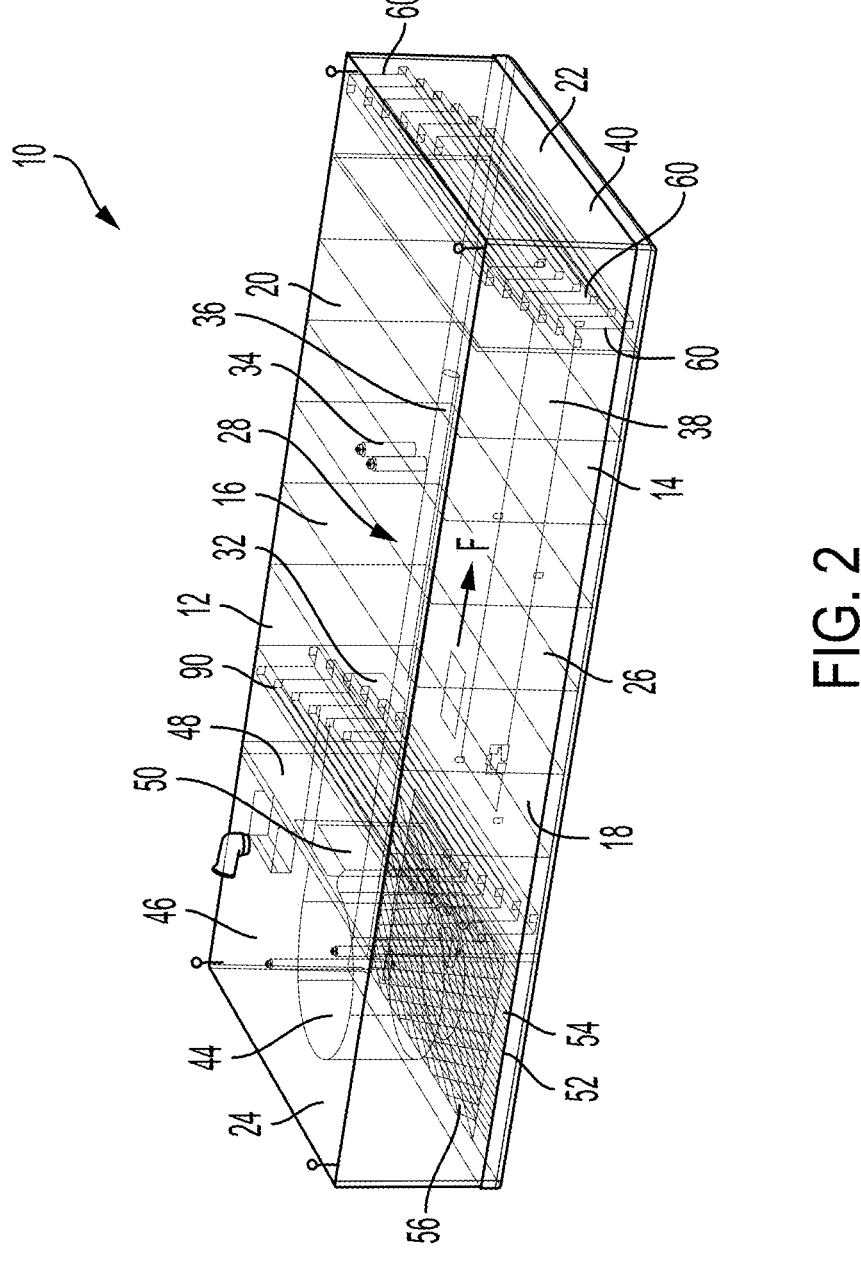
FIG. 2 is a perspective view of the air purifier of FIG. 1 with the parts shown in transparent to illustrate the basic structures thereof.

The air purifier 10 of the present application is of the type designed to be mounted in or a ceiling or wall. That is, the purifier 10, for example, can be mounted inside a wall (structures inside a wall are also commonly referred to as behind the wall), such in the gap between two drywall sheets, inside a modular office furniture wall, or the like. The air purifier 10 can also be mounted on an exterior surface of a ceiling or wall facing into the room, including suspended below a ceiling surface, e.g., by cables, chains, rods or other flexible or rigid supports. The purifier 10 can also be mounted inside a ceiling (also called within or above the ceiling), such as in the space above a drop ceiling, in attic space above a residential ceiling made of drywall or the like, and so on. The specific application is not intended to be limiting, and these examples are intended to provide just some possible installation options.

The air purifier 10 comprises a housing 12 for installation in or on a wall or ceiling of a room. The air purifier 10 may also be installed in any building space, including rooms, hallways, storage spaces, manufacturing areas, common spaces, etc. The housing 12 may have any construction or configuration, and the illustrated design is not intended to be limiting. The housing 12 may have any hardware or mounting structure suitable for mounting it in its installation location, which will typically vary based on the installation location. Hardware or other mounting structure for devices in or on walls or ceilings are well-known in the art and need not be detailed.

In the illustrated embodiment, the housing 12 has a generally rectangular shape with first and second generally parallel main walls 14, 16 and side walls 18, 20, 22, 24 connecting the main walls 14, 16 to enclose the interior space. The corresponding pairs of side walls 18, 20, 22, 24 are essentially parallel to one another also. The illustrated, non-limiting design is designed to be installed in a drop ceiling, which are commonly found in offices and other types of rooms, and may occupy, e.g., the length of two tiles of a typical drop ceiling. The main wall 14 may be designed to be placed directly on top of a drop ceiling tile or tiles so as to be concealed, or may be designed to take the place of a drop ceiling tile or tiles so as to be exposed (i.e., occupy the space in the drop ceiling framing that would otherwise be occupy by the tiles). The same design can likewise be used in or on a drywall ceiling or wall, or any other installation location.

For examples of non-limiting dimensions, in a drop-ceiling application, the housing 12 may have a length (in the flow direction) between 47 and 48 inches, more preferably between 47$\frac{3}{16}$ and 47$\frac{7}{8}$ inches, and even more preferably 47$\frac{7}{8}$ inches. The illustrated embodiment has a length of 47$\frac{7}{8}$ inches. The housing 12 may also have a width (in the direction between walls 18, 20, i.e., perpendicular to the page of FIG. 1) between 23 and 24 inches, more preferably between 23$\frac{3}{16}$ and 23$\frac{7}{8}$ inches, and even more preferably 23$\frac{7}{8}$ inches. The illustrated embodiment has a width of 23$\frac{7}{8}$ inches. The housing 12 may also have a height (in the direction between walls 14, 16, i.e., vertical in FIG. 1) between 8 and 15 inches more preferably between 8 and 10 inches, and even more preferably between 8 and 8$\frac{1}{2}$ inches. The illustrated embodiment has a height of 8$\frac{1}{8}$ inches. Larger and smaller dimensions may be used for all these dimensions.

Figure 10:
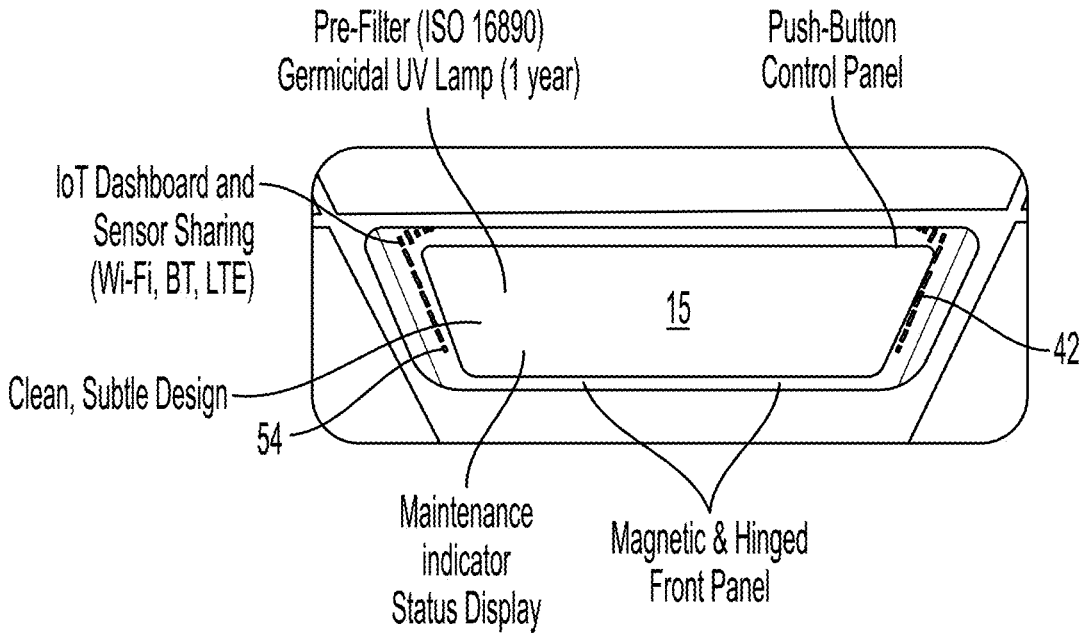
FIG. 10 is a bottom perspective view of an air purifier, such as one constructed in accordance with FIG. 1, showing the purifier mounted in a drop ceiling with a cover included.

The materials used to construct the housing 12 may of any type. In the illustrated embodiment, the housing 12 may be constructed from sheet metal components secured together. If the housing 12 is designed to be exposed, e.g., where it is mounted in place of a drop-ceiling tile or tiles, the main wall 14 that is facing the room may be coated, painted, made of plastic, or configured in any other way to improve its aesthetic appearance. As another example, the main wall 14 may have an aesthetic façade piece attached to it. For example, FIG. 10 shows an embodiment installed in place of a drop-ceiling tile having a façade piece in the form of a cover 15 mounted beneath the main wall 14. The cover 15 may be secured in place in any suitable manner, such as by magnetic mounting, snap-fit attachment, latches, retainers, screws, etc. The cover 15 may be entirely removable, or it may be mounted to the main wall 14 by a hinge so that it can swing away from the main wall 14 to uncover it for servicing of the purifier 10.

The housing 12 includes a UV light sterilizing chamber 26 in the housing 12, which directs the flow of air therethrough in a flow direction F extending between first and second opposing ends of the chamber 26. The flow direction F is preferably essentially parallel to the first main wall 14 so as to be essentially parallel to the surface of the wall or ceiling in which it is installed. The flow direction is understood by a person of ordinary skill in the art as the major direction over which flow occurs, it being understood that the flow field itself may have some amount of curvature or turbulence and that actual flow in real-life is typically not perfectly aligned in a single direction. The flow direction F may also be referred to as the main axis or longitudinal direction of the chamber 26, as that is the major direction of the flow.

In the illustrated embodiment, both walls 14 and 16 are essentially parallel, which helps encourage laminar flow in the flow direction F. The inventors have recognized that, while turbulent flow allows for some parts of the air flow to remain exposed to the UV sterilizing light for longer (such as recirculation spots and dead zones), that may provide little or no additional benefit, while other parts that are more laminar and flow past the turbulent areas may be exposed for less time and may not benefit sufficiently from the sterilizing effect of the radiation. Also, having turbulent flow can decrease the turnover efficiency/flow rate of the device overall. Thus, the inventors have recognized that turbulent flow is not as effective and found that laminar flow is more advantageous from a consistency standpoint in terms of exposure time to the radiation and management of the flow rate/device turnover because it has less dead zones or areas of recirculation that effect the overall flow rate and air turnover.

For examples of non-limiting dimensions, in a drop-ceiling application, the sterilizing chamber 26 may have a length (in the flow direction) between 34 and 38 inches, more preferably between 34 and 36 inches, and even more preferably between 34 and 35³⁄₁₆ inches. The illustrated embodiment has a length of 35³⁄₁₆ inches. The sterilizing chamber 26 may also have a width (in the direction between walls 18, 20, i.e., perpendicular to the page of FIG. 1) between 23 and 24 inches, more preferably between 23½ and 23¾ inches, and even more preferably 23⅝ inches. The illustrated embodiment has a width of 23⅝ inches. The sterilizing chamber 26 may also have a height (in the direction between walls 14, 16, i.e., vertical in FIG. 1) between 7¾ and 15 inches, more preferably between 8 and 10 inches, and even more preferably 8 inches. The illustrated embodiment has a height of 8 inches. Larger and smaller dimensions may be used for all these dimensions.

A UV light source 28 is mounted in the sterilizing chamber 26 for emitting UV light to sterilize air flowing through the sterilizing chamber 26. The UV light source 28 is of a conventional construction and has a ballast 30 with a power source that connects to a source of electrical power (typically building AC power) and mounting connections, such as brackets 32, 34. A UV bulb 36 that is powered to emit the UV radiation is connected to the ballast 30 for delivery of the electricity and mounted to the brackets 32, 34. The UV bulb 36 in the illustrated, non-limiting embodiment is oriented in the flow direction F so as to extend in the direction between the first and second ends of the housing 12. This orientation advantageously increases the exposure time of the UV radiation to the flow of air through the sterilizing chamber 26, especially due to the enhanced laminar flow provided herein.

The UV light source 28 may be mounted to the main wall 16, on which the ballast 30 and brackets 32, 34 are located. The other main wall 14 facing the room/space includes an access panel 38 that covers an access opening and is removable therefrom so the UV bulb 36 and any related components can be accessed for replacement when necessary. The access panel 38 may be removably secured by any suitable fastener mechanism, such as screws through openings in the access panel 38 and the edges of the main wall, snap-fit connections, slide locks, or the like. The access panel 38 may be entirely removable, or may be removed by pivoting to about a hinge. The construction and configuration is not intended to be limiting.

The brackets 32, 34 illustrated may be formed of plastic, metal, or any other suitable material and have a sheet or plate-type design. The brackets 32, 34 may be oriented so that the thickness of the plate or sheet material is oriented in the flow direction F so as to be more aerodynamic and reduce creation of turbulence in the flow within the sterilizing chamber. Another example would be to use rods or wires for suspension of the bulb, which likewise have a low-profile to the air flow. The design illustrated is not intended to be limiting, and any mounting configuration may be used.

The UV radiation spectrum or wavelength used may be selected to kill pathogens, like bacteria and viruses, which may vary depending on the particular environment. Generally, the UV-C spectrum (200-280 nm) is effective for killing bacteria and viruses. A wavelength of 254 nm may be used in that spectrum, or a broader range in that spectrum including 254 nm may be used. Embodiments of the invention may also use UV radiation in the Far-UV spectrum, which is a sub-set of UV-C in the range of 207-222 nm also. Some other embodiments may use a broader range, including a combination of wavelengths or wavelength ranges within any of the UV-A, UV-B, and/or UV-C spectrums, which may have the benefit of efficacy against a wider range of pathogens. Any such UV wavelength or range of wavelengths used for killing pathogens may be generally referred to as pathogenic UV radiation. The challenge with UV radiation is that the amount used, and spectrums selected, can also be problematic when exposed to human skin and/or eyes, so the amount that leaks or escapes from the purifier 10 should be limited or eliminated.

Although the illustrated embodiment is shown with a single UV light source 28, some embodiments may have multiple ones. For example, in an embodiment two UV light sources 28 (or more) may be used. In such embodiments, the multiple UV light sources 28 may be parallel to one another. When multiple light sources 28 are used, one non-limiting option is to have the different bulbs 30 emit at different wavelengths or ranges of wavelengths to increase the spectrum coverage. Further, instead of bulbs, other UV light sources, such as LEDs can be used, and the LEDs used may likewise emit the same wavelengths or different wavelengths/ranges of wavelengths to increase the spectrum coverage.

The inner surfaces of the sterilizing chamber 26 may have a reflective characteristic to increase the exposure of the UV radiation to the air flowing therethrough. By reflective characteristic, this is defined and understood as meaning the surface has the ability to reflect the UV radiation being emitted by the source, or at least sub-set of its spectrum range with pathogenic efficacy.

The reflective characteristic may be provided by coating the inner surfaces of the sterilizing chamber 26 with a reflective material. An example of such a reflective coating material may include, but is not limited to aluminum, PTFE, or any other material that reflects the UV light. Another example may be to mount panels coated with such a reflective coating material, or made from a reflective metal or other material, on the inside of the housing 12 within the sterilizing chamber 26 or to construct parts of the housing 12 defining the sterilizing chamber 26 from such panels. An example of a panel made from reflective metal material may be one made from Alanod Micro-UVC material from Alanod, Ltd. in the U.K. Other examples are to use polished metal, such as anodized aluminum, metal plating, etc. Preferably, the spectral light reflectivity of the reflective surface (of whatever type) is greater than 70%, more preferably greater than 80%, and still more preferably greater 90% for the UV radiation emitted (or at least a sub-set of its spectrum range with pathogenic efficacy).

As will become more apparent from the discussion below concerning the use of baffles to address UV light leakage, in an embodiment the surfaces inside the sterilizing chamber 26 which are provided with the reflective characteristic may be some or all of those surfaces shown as extending in the flow direction F, i.e., the surfaces of the main walls 14, 16 and side walls 18, 20. The use of baffles is done to prevent the UV light, including from increased reflection, from being directed towards the ports discussed below, and reduce UV light leakage.

A first port 40 is provided on the housing 12. This port 40 is communicated to the UV light sterilizing chamber 26 at the first end thereof for permitting flow of the air between the sterilizing chamber 26 and the room via the UV chamber port 40. Thus, it may also be referred to as a UV chamber port 40, which term is used as a matter of convenience to denote that it is the port at the end not associated with the fan discussed below; it may include additional structures and need not be directly connected to the sterilizing chamber 26 where the UV bulb 36 is located. The UV chamber port 40 is oriented at an angle to the flow direction F for facing the room. In the illustrated non-limiting embodiment, the UV chamber port 40 is oriented essentially perpendicular to the flow direction F (i.e., it faces perpendicularly to the flow direction). The port 40 may have any shape, design or configuration. In the illustrated embodiment, the port 40 is an opening in the first main wall 14 at the end of the housing 12, which is covered by a grill 42. The grill 42 may be removable or permanently integrated in the housing. This design is not intended to be limiting, and the port 40 may have any construction or configuration that allows air to flow therethrough between the chamber 26 and the room.

Because the UV chamber port 40 is provided adjacent the housing end wall 22, as an option that wall 22 is not designed to be reflective in the manner discussed above. Having that end wall 22 be reflective would increase the probability of UV light incident thereon from reflecting off its inner surface and leaking through the UV port 40. Likewise, as an option, the inner surfaces on the portions of the walls 14, 16, 18, 20 adjacent the UV port 40 (i.e., at or beyond the associated baffles discussed below) are also preferably not made reflective for the same reason. In some embodiments, one or more of these surfaces of the wall 22 or wall portions 14, 16, 18, 20 beyond the baffles 60 may be anti-reflective in the same manner discussed below with respect to the baffles 60.

The purifier 10 includes a fan 44 for generating the flow of the air from the room and through the UV light sterilizing chamber 26 and UV chamber port 40. The fan 44 is distal from the UV chamber port 40. In the illustrated embodiment, the fan 44 is positioned within a fan chamber or plenum 46 included in the housing 12 adjacent the second end of the sterilizing chamber 26. The fan chamber 46 has a wall 48 between the fan chamber 46 and the sterilizing chamber 26. The wall 48 isolates the fan chamber 46 from the sterilizing chamber 26 and has an opening 50 for communicating the fan chamber 46 and the sterilizing chamber 26. Thus, airflow between the chambers 26 and 46 is through the opening 50.

Figure 14:
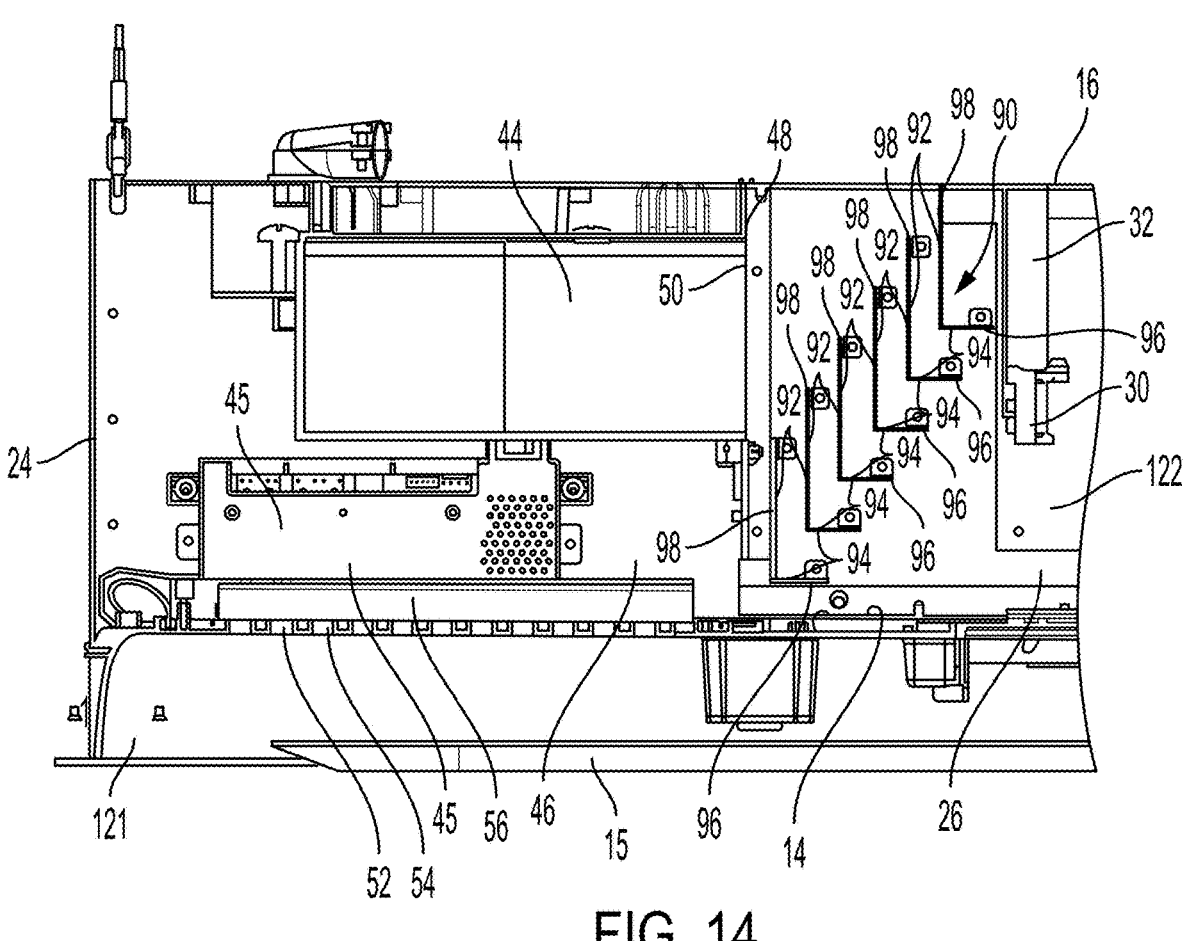
FIG. 14 is a view similar to FIG. 4 with additional structural details.

The fan 44 may be of any type, and the illustrated design has a centrifugal or mixed flow fan. The particular type of fan 44 used is not intended to be limiting. A single fan 44 is preferably used, but multiple smaller fans 44 may be used also. The fan 44 may have an integrated motor, or a separate motor 45 and controller system (FIG. 14).

A second port 52 on the housing 12 is communicated to the UV light sterilizing chamber 26 at the second end thereof for permitting flow of the air between the sterilizing chamber 26 and the room via the second port 52. In the illustrated embodiment, the communication is through the fan 44 and the opening 50 in wall 48, and the interior of the fan chamber 46 may also be included in the communication path. Thus, this second port 52 may also be referred to as the fan port 52. Like the UV chamber port 40, the fan port 52 is oriented at an angle to the flow direction F for facing the room, and in the illustrated embodiment is oriented perpendicular to the flow direction. The port 52 may have any shape, design or configuration. In the illustrated embodiment, the port 52 is an opening in the first main wall 14 at the end of the housing 12 associated with the fan chamber 46, which may be covered by a grill 54. The grill 54 may be removable or permanently integrated in the housing. This design is not intended to be limiting, and the port 52 may have any construction or configuration that allows air to flow therethrough between the chamber 26 and the room.

In the illustrated embodiment, the fan 44 is configured to draw the flow of air in from the room through the fan port 52 and deliver the flow of air through the sterilizing chamber 26 and back out to the room through the UV chamber port 40. Thus, the UV light source 28 in the chamber 26 is able to sterilize the air flowing therethrough by exposure to the UV radiation. The direction of flow is not critical, and it is also possible for embodiments to be designed such that the air flows in an opposite direction, with the fan applying negative pressure to the sterilizing chamber 26 so that air is pulled in through the UV chamber port 40 and expelling the air under positive pressure through the fan port 52.

In the illustrated embodiment where the fan 44 draws the flow of air in from the room through the fan port 52, a filter 56 may be mounted in the fan port 52. The filter 56 removes particulates from the air prior to entering the fan 44 and the sterilizing chamber 26, thus reducing the collection of particulates within the purifier 10. This type of filter is commonly called a pre-filter because it filters the air before subsequent purifying. The type of filter used is not intended to be limiting, and may for example include a HEPA filter. HEPA filters have the advantage of capturing some pathogens, and thus reducing the amount that needs to be sterilized. However, any type of filter may be used. For example, a carbon filter may also be used for removing odors and VOCs. If a grill 54 is used, the filter 56 may be mounted in the fan port 52 and covered by the grill 54. Likewise, the filter 56 may be mounted in place without the use of a grill.

Figure 3:
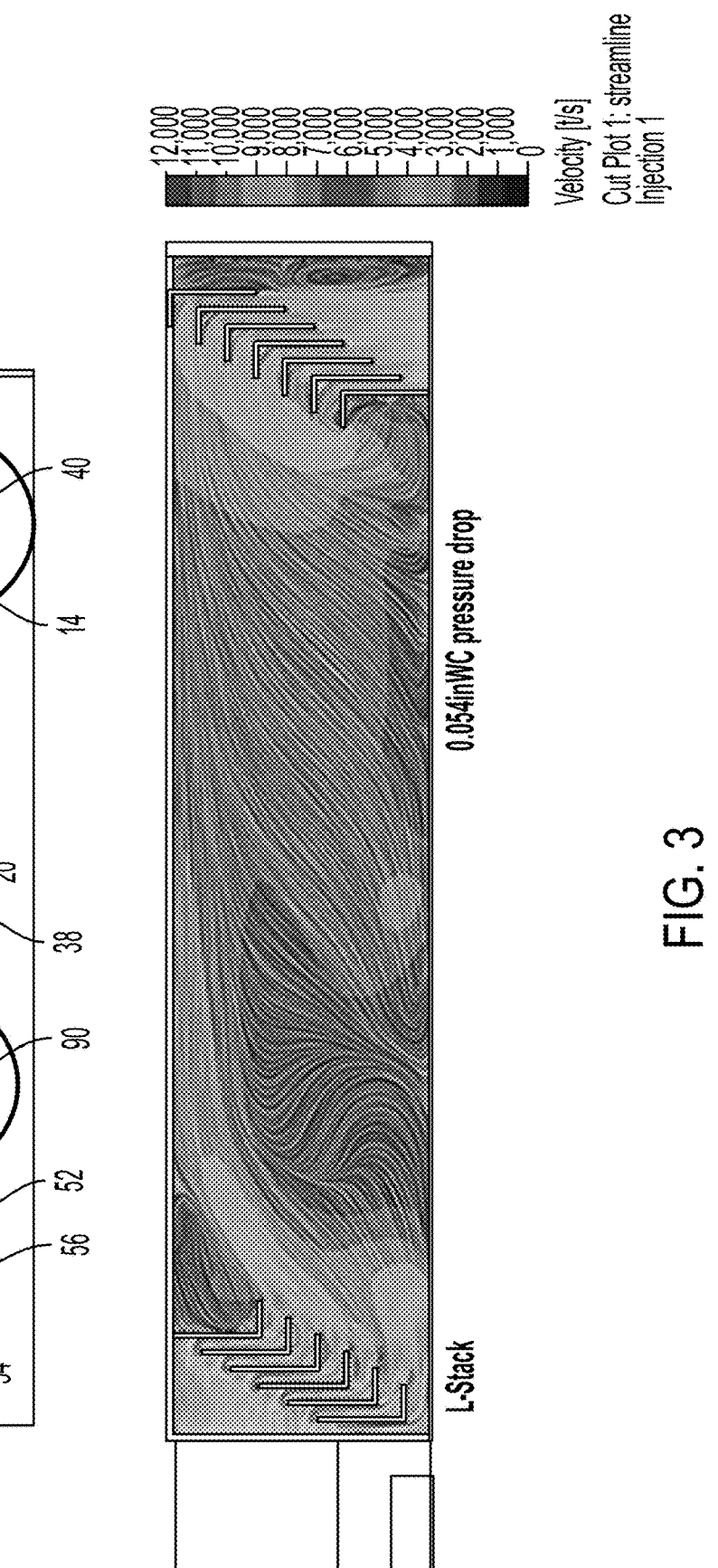
FIG. 3 is a view similar to FIG. 1, with partial perspective included, and a call-out to illustrate an example of the flow pattern in the sterilizing chamber.

The purifier 10 has a plurality of baffles 60 mounted adjacent the UV chamber port 40. The baffles 60 provide a series of port guiding surfaces 62 oriented towards the UV chamber port 40 for directing the air flowing between the sterilizing chamber 26 and the UV chamber port 40 in the direction of the UV chamber port 40. More specifically, the port guiding surfaces 62 are configured to direct the air flowing between flow channels defined between the baffles 60 and the port 40. As will be discussed below, the surfaces 62 do not need to be oriented in the exact direction of the chamber port 40 (i.e., precisely perpendicular to the flow direction F in the illustrated embodiment), and being oriented generally in that direction may be sufficient in some embodiments. The term generally is used to mean that a part or surface is oriented at an angle that has a substantial component (in a vector sense) in a particular direction. A structure that extends exactly or very close to that direction is considered essentially in that direction, and a structure that has a substantial component (up to and including 45 degrees) would be considered being generally in that direction. The baffles 60 also provide a series of chamber guiding surfaces 64 oriented generally in the flow direction F for directing the flow of the air for directing flow in the sterilizing chamber 26. In the illustrated embodiment, the flow is directed towards the baffles 60, and thus the chamber guiding surfaces 64 function to direct flow by collecting or receiving the flow of air generally in the flow direction F into the series of baffles 60. That is, the chamber guiding surfaces 64 are configured to direct the air flowing between the flow channels between the baffles 60 and the sterilizing chamber 26. In the illustrated embodiment, the chamber guiding surfaces 64 may also optionally direct the flow in a manner that encourages or induces laminar flow in the field being received from the chamber 26 by the baffles 60, which reduces turbulence within the chamber 20. FIG. 3 shows how the flow is more laminar as it enters the baffles 60, which in part is encouraged by the orientation of the chamber guiding surfaces 64. The flow field shown shows a significant amount of laminar flow in the air of the UV bulb, which is advantageous for ensuring a consistent exposure to UV light for the air volume passing through.

The terms port guiding surfaces and chamber guiding surfaces are used for convenience to identify the roles of these surfaces in directing flow to/from the chamber or a port, respectively. The term directing is used to include guiding the direction of air flow leaving the baffles and guiding the direction of air flow entering the baffles, including collecting air (e.g., from the sterilizing chamber 26 into the baffles). Also, the terms first and second are used for convenience to denote walls or surfaces of the baffles (or any other structures), and do not denote any particular order, maximum number or any other significance.

In the illustrated, non-limiting embodiment, each baffle 60 of the plurality thereof includes a first baffle wall 66 extending towards the sterilizing chamber 26 and a second baffle wall 68 extending toward the UV chamber port 40. Thus, the first baffle walls 66 provide the chamber guiding surfaces 64 and the second baffle walls 68 provide the port guiding surfaces 62. As illustrated, each baffle 60 of the plurality thereof has the first and second walls 66, 68 thereof connected to one another, and the connection may be by forming the baffle 60 as one continuous, integral piece, such as bent sheet metal, molded plastic, or other like. In the non-limiting illustrated embodiment, each baffle 60 of the plurality thereof is L-shaped with the first and second walls 66, 68 essentially perpendicular. As shown, the plurality of baffles 60 are oriented such that the first baffle walls 66 are essentially parallel to the flow direction F and the first main wall 14 of the housing 12, and the second baffle walls 68 extend towards the UV chamber port 40 essentially perpendicular to the first main wall 14 of the housing 12. The specific configuration illustrated is not intended to be limiting, and any baffle configuration may be used.

Figures 4, 5:
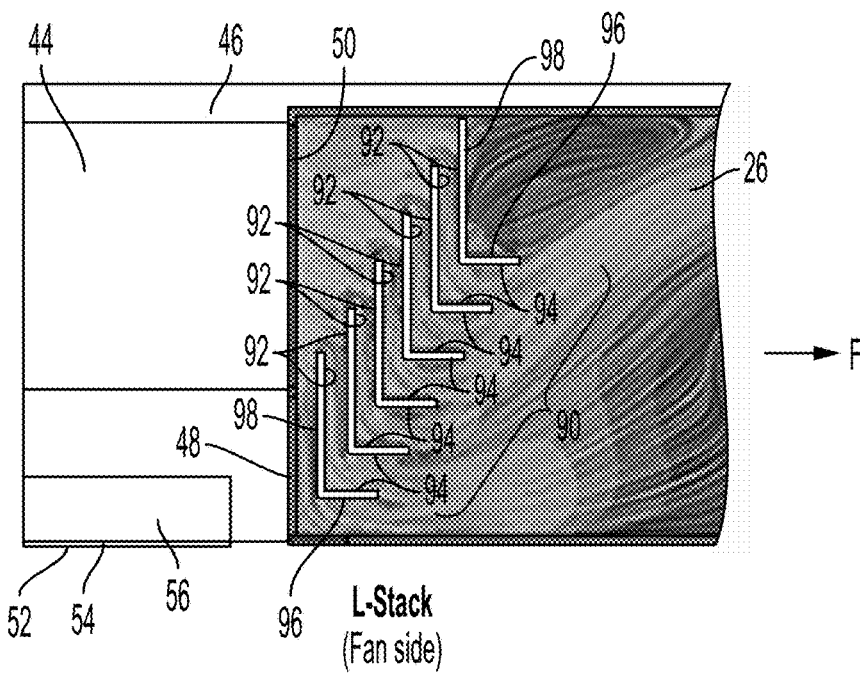
FIG. 4 is a partial close-up view of baffles used on a fan side of the sterilizing chamber in the air purifier of FIG. 1.
FIG. 5 is a partial close-up view of baffles used on the other side of the sterilizing chamber.
Figure 6:
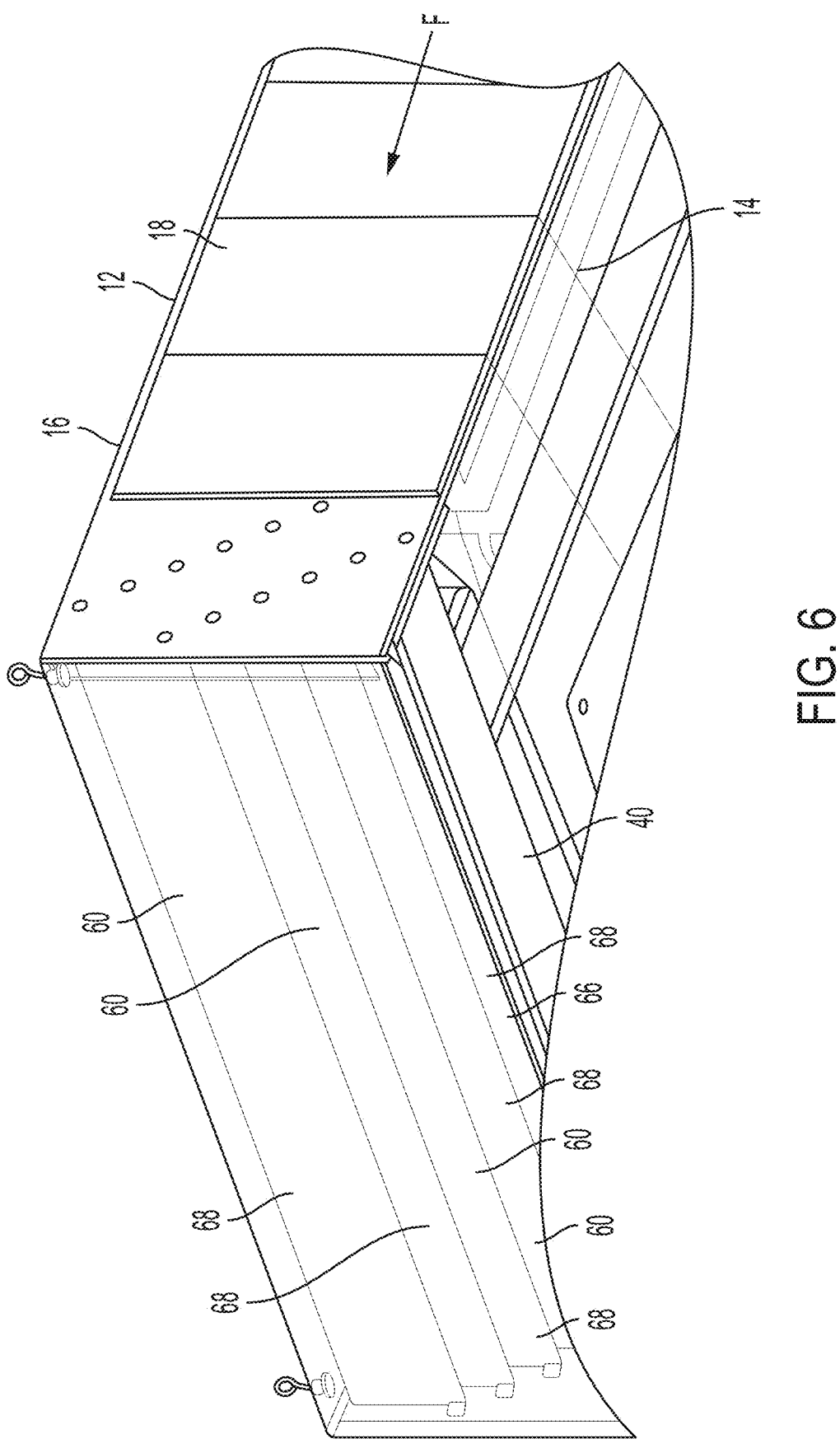
FIG. 6 is a partial perspective view taken from below the air purifier of FIG. 1 with an end wall transparent to illustrate the arrangement of baffles.

As shown, the plurality of baffles 60 are arranged in a stepped, nested, spaced apart arrangement. That is, they are spaced apart from one another so air can flow between the baffles, and nested with parts overlapping for compactness and to limit UV light leakage (as discussed below). Specifically, the first walls 66 of adjacent baffles 60 overlap each other in a spaced apart manner and the second walls 68 overlap each other in a spaced apart manner. The arrangement is referred to as stepped because the baffles extend somewhat diagonally, offset from one another in the vertical and horizontal directions of the cross-sections. As can be seen in FIG. 5 for example, the stepped arrangement extends generally diagonally away from the first main wall 14 (on which port 40 is located) and towards the adjacent end wall 22 (i.e., up and to the right in FIG. 5).

The baffles 60 in the illustrated design also provide the additional function of reducing or eliminating the escape of UV radiation through the UV port 40. To help with that function, the baffles 60 of the plurality thereof may have anti-reflective surfaces that reduce or eliminate reflection of the UV light emitted by the UV light source to reduce or eliminate emittance through the UV chamber port 40.

As the UV light is incident on a baffle surface, if the surface is sufficiently reflective, the radiation may be reflected directly or indirectly towards UV chamber port 40, allowing it to be emitted from the port 40 (leakage). By using anti-reflective surfaces, this can be reduced or eliminated. For example, by having the inner surfaces 62 of the second walls 68 that face in the direction of the light source 28 be anti-reflective, the radiation incident at an angle on those surfaces is not reflected (or its reflectance is significantly reduced), thus limiting the radiation directed to the UV chamber port 40. Additionally, having either or both surfaces 64 of each first wall 66 be anti-reflective as an additional option will likewise eliminate or reduce the radiation reflected off those surfaces toward the UV port 40 (including radiation that would reflect off them onto the inner surfaces of walls 68). Similarly, by having the outer surfaces 62 of walls 68 be anti-reflective, that can provide further reduction of reflection towards the UV port 40. Although radiation from the bulb 30 is not directed at those outer surfaces, to the extent any amount of radiation is reflected thereon off a second wall 68 or the inner surface of a first wall 66, having those outer surfaces 62 of the baffles 60 be anti-reflective as a further option helps limit the amount of UV radiation leakage through the UV chamber port 40.

In the illustrated embodiment, the baffles 60 preferably extend the entire width of the purifier in the width direction transverse to the flow direction F (i.e., perpendicular to the cross-section of FIG. 1), and their arrangement preferably extends in the entire height direction also (i.e., in the vertical direction of FIG. 1). Their mounting may be by any suitable means, such as brackets, fasteners, snap-fit connections, adhesive, or the like.

In the illustrated embodiment, an additional baffle wall 70 is provided adjacent the baffle 60 closest the UV chamber port 40. That additional baffle wall 70 is optionally used to block UV radiation from escaping past the edge of the second wall 68 of that baffle 60. The additional baffle wall 70 is also spaced from the second wall 68 of that baffle 60 to allow air to escape therebetween to limit the amount of turbulence or backflow in that region.

The baffle 60 surfaces discussed above may be made anti-reflective in any suitable manner. By anti-reflective, that term is defined as meaning limiting or eliminating reflectance of at least UV radiation, and the anti-reflectance property may be tailored to specific wavelengths of wavelength ranges of UV for which reflectance is desired to be avoided or eliminated. For example, the anti-reflectance may be targeted to limiting the reflectance of UV-C radiation, or a specific sub-set of wavelengths therein. Likewise, it may be targeted to limiting a wide range of UV radiation, including UV-A, UV-B, UV-C, or any combination thereof or wavelengths thereof (which are also discussed above). The radiation wavelengths targeted may likewise be dictated by the bulb 30 used for the UV radiation source (as not every bulb type emits the full UV spectrum, and thus there may be no concern with being anti-reflective with respect to wavelengths not emitted or emitted in negligible amounts).

One example of providing an anti-reflective surface is to coat the baffles surfaces with a coating that is anti-reflective. Examples of such coatings include titanium oxide (particularly for UV-C), Nanomyte, or a paint coating with polymer additives. Anti-reflective films are also considered coatings as that term is used herein. Another example is to make the baffles or parts thereof from a material that is anti-reflective, such that no coating needs to be added. Preferably, the spectral light reflectivity for the anti-reflective coating or other material (with respect to the UV radiation) is less than 15%, more preferably less than 10%, more preferably less than 5%, and still more preferably less than 1%. Preferably, this same reflective percentages/ranges may be for a specific sub-set of UV radiation, such as UV-C or a sub-set thereof emitted by the bulb 36, which is considered more harmful.

With the illustrated design with the particular arrangement of baffles used, because radiation will generally have to reflect off two or more surfaces before reaching the UV port 40, the anti-reflectivity will generally "stack up." For example, if the light reflects off two surfaces of 10% reflectivity, collectively the reflectivity is 1% because the first surface reflects 10% of radiation, and then the second surface reflects 10% of that 10%, i.e., 1%; if three reflections happen it is 0.1%, and so on. Thus, even anti-reflective materials that are less efficient may achieve an overall high amount of anti-reflection where the geometry dictates multiple reflections therefrom are needed to exit the port 40.

As mentioned above, the inner surfaces on the portions of the walls 14, 16, 18, 20 adjacent the UV port 40 (i.e., at or beyond the associated baffles 60) are also preferably not made reflective. In some embodiments, those surfaces may also have anti-reflective surfaces to eliminate or reduce further reflectance of UV radiation that escapes past the baffles 60. This is an option, and may not be a necessary feature if the baffles 60 provide sufficient protection against UV radiation leakage.

In addition, other joints, gaps, connection points or the like on the housing 12 may be provided with material to block UV light leakage. For example, the access panel 38 or the opening in which it is received may be provided with a seal or gasket to limit or eliminate escape of UV light. Similarly, areas where the housing walls are joined may be sealed with trim seal, tape, opaque caulking or the like. The same may be done for any holes where fasteners are mounted. These additional features for blocking escape of UV radiation are optional and not intended to be limiting.

Figure 11:
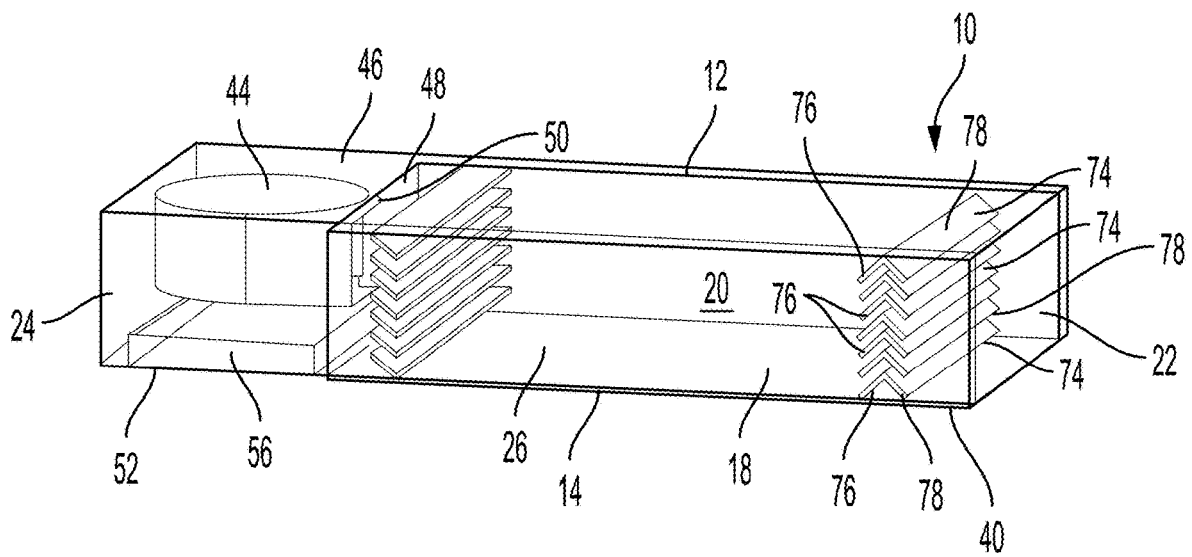
FIG. 11 is a view similar to FIG. 3 using alternative baffles.

FIG. 11 shows a cross-section using baffles 74 with an alternative design having first and second baffle walls 76 arranged in a V-shaped configuration. The plurality of baffles 74 are oriented such that the first baffle walls 76 extend at a first angle with respect to the flow direction towards the first main wall 14 of the housing 12 and the sterilizing chamber 26, and the second baffle walls 78 extend at a second angle with respect to the flow direction F toward the first main wall 14 of the housing 12 and the UV chamber port 40. That is, the angles are non-perpendicular to the flow direction F (and the main wall 14) and diverge from one another so the V-shape opens/faces in the direction of the first main wall 14 and the UV chamber port 40. Although the surfaces of the first and second baffle walls 76, 78 (their chamber guiding and port guiding surfaces, respectively) are not oriented parallel to the flow direction F and the direction of the port 40, they are oriented generally in those directions. The plurality of baffles 74 are arranged in a nested, spaced apart arrangement with the first walls 76 of adjacent baffles 74 overlapping each other in a spaced apart manner and the second walls 78 overlapping each other in a spaced apart manner. This design does not have the stepped arrangement of the prior embodiment.

Figure 12:
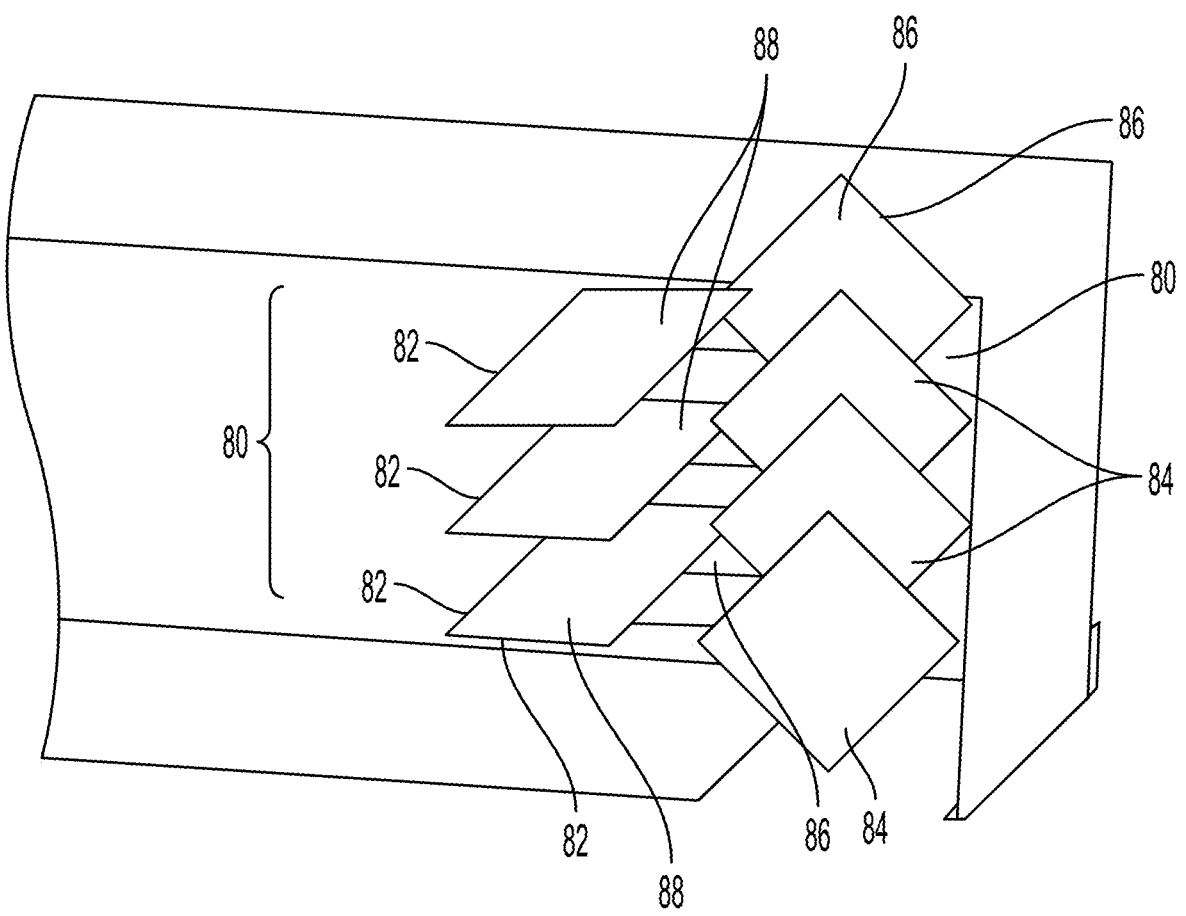
FIG. 12 is a view similar to FIG. 5 using additional alternative baffles.

FIG. 12 shows another cross-section with baffles 80 having another alternative design. The plurality of baffles 80 are oriented such that the first baffle walls 82 extend essentially parallel to the first main wall 14 (also in the flow direction) and the sterilizing chamber 26 (like the first embodiment discussed), and the second baffle walls 84 extend at an angle with respect to the flow direction toward the first main wall 14 and the UV chamber port 40 (like the second embodiment discussed). As illustrated, the plurality of baffles 80 are arranged in a nested arrangement with the first walls 82 of adjacent baffles 80 overlapping each other in a spaced apart manner and the second walls 84 overlapping each other in a spaced apart manner.

Optionally, the first and second walls 82, 84 of each baffle 80 of the plurality thereof are connected by at least one intermediate wall, and the plurality of baffles 80 are arranged in a nested arrangement with the first walls 82 of adjacent baffles 80 overlapping each other in a spaced apart manner, the second walls 84 overlapping each other in a spaced apart manner, and the intermediate walls overlapping each other in a spaced apart manner. In the non-limiting, illustrated embodiment, the at least one intermediate wall includes a third wall 86 that is essentially parallel to the first wall 14 of the housing 12 (and the flow direction F) and connected to the second wall 84, and a fourth wall 88 that extends at a first angle with respect to the flow direction F towards the first main wall 14 and the sterilizing chamber 26 and that is connected to the first wall 82 and the third wall 86. As one advantage, this provides additional surface area for incident UV radiation to be absorbed due to repeating reflection.

In each of these alternative baffle designs (or any other baffle design), the surfaces thereof may be anti-reflective in the same manner as discussed above, which need not be repeated.

In the illustrated embodiment, a second plurality of baffles 90 are mounted adjacent the fan port 52 (and if used the previously discussed baffles on the UV side may be regarded as a first plurality). The baffles 90 of the plurality are shown in the non-limiting illustrated embodiment as being in the sterilizing chamber 26 adjacent the inner surface of wall 48. As will be discussed, this enables the baffles 90 to collect the air leaving the fan 44 through the opening 50 in the fan chamber wall 48 and direct a more laminar flow of air into the sterilizing chamber 26 toward the opposing baffles at the other end of the chamber 26.

In the illustrated embodiment, the baffles 90 have the same configuration as the baffles used at the other end of the sterilizing chamber 26, and as illustrated in the non-limiting FIGS. 1-6 they are shown as the same as baffles 60. The baffles 90 may be optionally inverted relative to the baffles 60 (i.e., so that the second walls 68, 98 thereof extend in opposing directions and the first walls 66, 96 extend towards one another), but that is not a limiting feature. The baffles 90 may have any other baffle configurations discussed herein, like baffles 70 and 80 used at the UV side. For example, FIG. 11 shows the same baffles as baffles 70 used at the fan side, which are arranged in an inverted manner so the V-shape open towards wall 16 instead of wall 14 (but may also be arranged in the same manner as the baffles 70). Similarly, the same baffles 80 in FIG. 12 may be used, such as with the baffles 80 flipped around the height axis so the walls 82 extend towards the UV chamber 26. Also, the baffles on the fan side may have any other construction or configuration, and the illustrated designs are not intended to be limiting. A non-limiting advantage of using baffles of the same type on both sides is cost-reduction from using more common components, but that is not a necessary feature to practice the invention.

The non-limiting illustrated baffles 90 of the second plurality provide a series of port guiding surfaces 92 for directing the air flowing between the fan 44 and the sterilizing chamber 26. These surfaces 92 do not need to extend in any particular direction, and as illustrated they are oriented perpendicularly to the flow direction F and the output direction of the fan, which puts them parallel to fan chamber wall 48 and perpendicular to the main wall 14. These surfaces 92 are still considered as oriented towards the fan 44 due to extending towards the fan 44 in the flow path from the fan 44 to the chamber 26. Having an orientation with a component perpendicular to the fan output provides the advantage of helping collect the flow from the fan in a more laminar manner. More specifically, because the air exiting the fan typically has a twisting or rotational component to its flow field due to the rotation of the blades (which is more pronounced in certain fans, like those of the mixed flow type), having the surfaces 92 oriented at an angle with respect to the flow direction, and preferably essentially perpendicular to it, helps reduce the rotational momentum imparted to the flow field exiting the fan 44 through the opening 50 as it enters the baffles 90. For example, with a centrifugal fan having a rotational axis in the vertical direction of FIG. 1 (i.e., perpendicular to both the flow direction F and the width direction) the air exiting the fan tends to flow radially out from the fan with respect to the fan axis. The radial component in the middle of the width direction tends to be more in the flow direction, while the radial component towards the side walls tends to be at an angle to the flow direction. The flow may also have a circumferential component as well due to the rotation of the fan. The baffles, and particularly the baffle surfaces 92, help collect the flow exiting the fan so it can be delivered from the baffles 90 in a more laminar manner in the flow direction F in the chamber 26.

The baffles 90 of the second plurality also provide a series of chamber guiding surfaces 94 oriented generally in the flow direction F for directing the flow of the air in the sterilizing chamber 26. Specifically, the chamber guiding surfaces 94 are preferably oriented in the flow direction F so that the flow collected by the baffles 90 and exiting therefrom is directed in a more laminar pattern.

Similar to the baffles 60, the baffles 90 of the second plurality are arranged in a spaced apart arrangement to provide a series of flow channels including the series of port guiding surfaces 92 and the series of chamber guiding surfaces 94. As discussed, the port guiding surfaces 92 are configured to direct the air flow between the flow channels and the fan 44 generating flow via the second port 52, and the chamber guiding surfaces 94 are oriented generally in the flow direction for directing the air flowing between the flow channels and the sterilizing chamber. The baffles 90 may each be L-shaped with a first wall 96 providing the laminar flow directing surfaces 94 and a second wall 98 providing the port guiding surfaces 92. As illustrated, the first baffle walls 96 may extend towards toward the sterilizing chamber 26 and the second baffle walls 98 extend generally or essentially perpendicularly to the main walls 14, 16 at outer ends of the first baffle wall 96. The walls 96 and 98 may be joined together as a single, continuous part, as discussed above with respect to the baffles 60. Again, any construction or configuration may be used for the baffles 90 and the illustrated design is not intended to be limiting.

In the illustrated embodiment, the baffles 90, like the other baffles discussed above, preferably extend the entire width of the purifier in the width direction transverse to the flow direction F (i.e., perpendicular to the cross-section of FIG. 1), and their arrangement preferably extends in the entire height direction also (i.e., in the vertical direction of FIG. 1). Their mounting may be by any suitable means, such as brackets, fasteners, snap-fit connections, adhesive, or the like. Also, as can be seen in FIG. 4, the baffles 90 are arranged in a stepped, nested and spaced apart arrangement. Specifically, the stepped arrangement extends generally diagonally away from the fan 44 and away from a first main wall 14 including the second port 52 (i.e., the diagonal direction is up and to the right in FIG. 4). FIG. 14 is an additional Figure showing additional structural features, including the fan 44 and associated components discussed herein.

In a non-limiting embodiment, the baffles 90 (or any other design) of the second plurality thereof have an anti-reflective surface, such as a coating, film or by an inherent property of the material used, the reduces or eliminates reflection of the UV light emitted by the UV light source to reduce or eliminate emittance through the fan port 52. The anti-reflective characteristic may be provided in the same manner as the other baffles discussed above and the above discussion applies equally.

On the fan side, the path for light to travel to the fan port 52 is typically more tortuous/complex, and includes the opening 50 on the chamber wall 48, the fan 44 itself, and any filter 56 or grill 54 used on the opening 52. UV radiation leakage is less likely to occur on the fan side, as it is more difficult for UV radiation to reflect off these various surfaces and exit the fan port 52, especially if a filter 56 is used that has low translucency to the UV radiation. However, it is still possible for UV leakage to occur, particularly if structures like the fan interior surfaces or the fan blades are made from a material that is highly reflective to the UV radiation. Thus, the use of the anti-reflective surface on the baffles at the fan side may have benefit, but can also be optional and may be omitted.

Similarly, if the configuration of the device is such that UV light leakage through the fan port 54 is not an issue, it is also possible to make the baffles at the fan side and/or the chamber wall 48 with a surface that is reflective to the UV radiation, similar to the sterilizing chamber surfaces discussed above, to increase the radiation intensity within the chamber. Even if UV leakage is not a concern, however, it still may be beneficial to shield the fan components from the UV radiation, as UV radiation, particularly in the UV-C spectrum, can have a degrading effect on materials over time, and particular on any plastics, rubber or the like used in the fan construction. Thus, the invention can be practiced with or without anti-reflective properties on the baffles or wall 48 at the fan side, and it may be used for reasons different from the UV side where there is a more direct path from the sterilizing chamber 26 to the UV side port 40.

Figure 7:
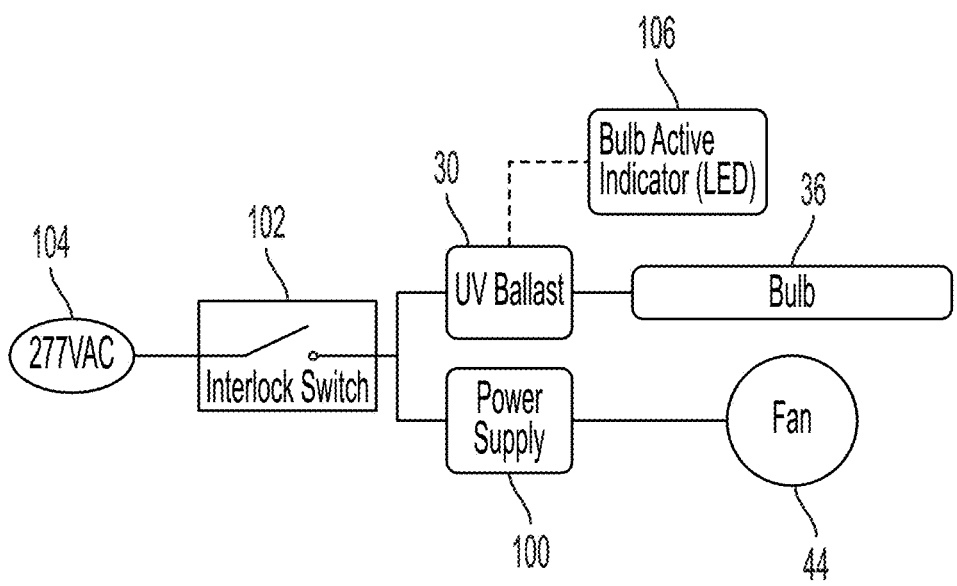
FIG. 7 is a schematic electrical diagram of an electrical system used in the air purifier of FIG. 1.
Figure 8:
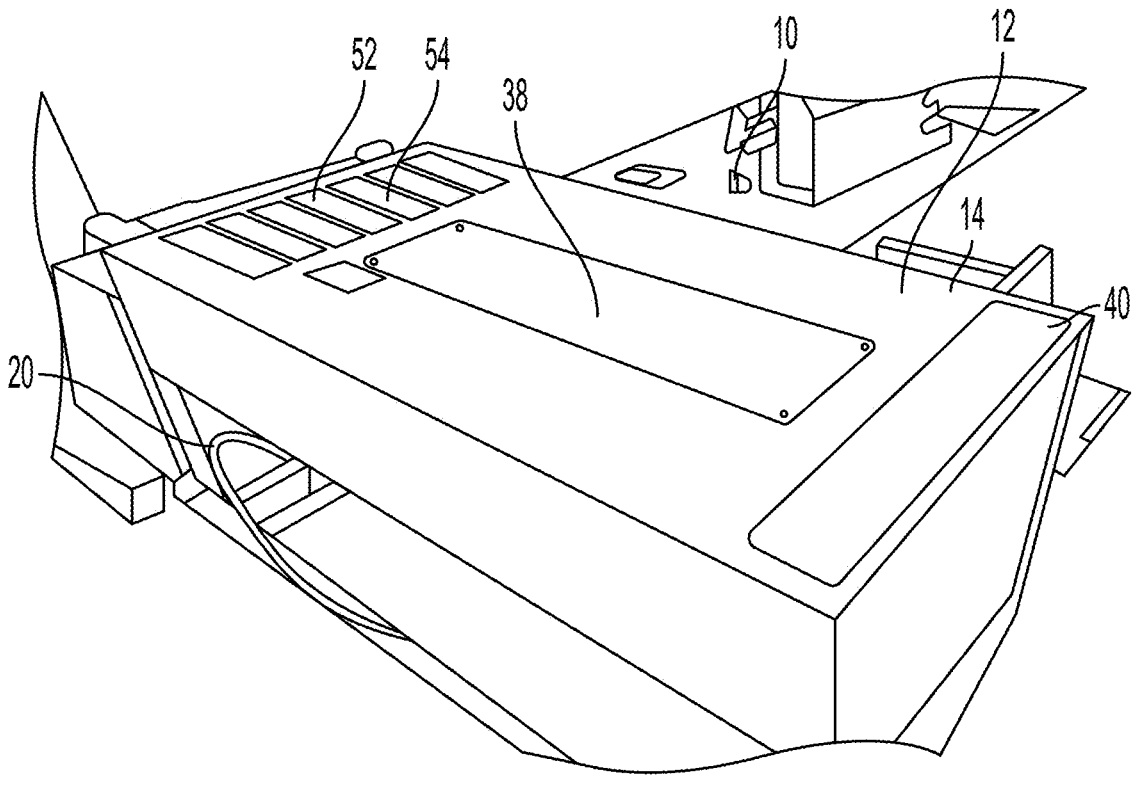
FIG. 8 is a bottom perspective view of a prototype air purifier constructed based on FIG. 1.
Figure 9:
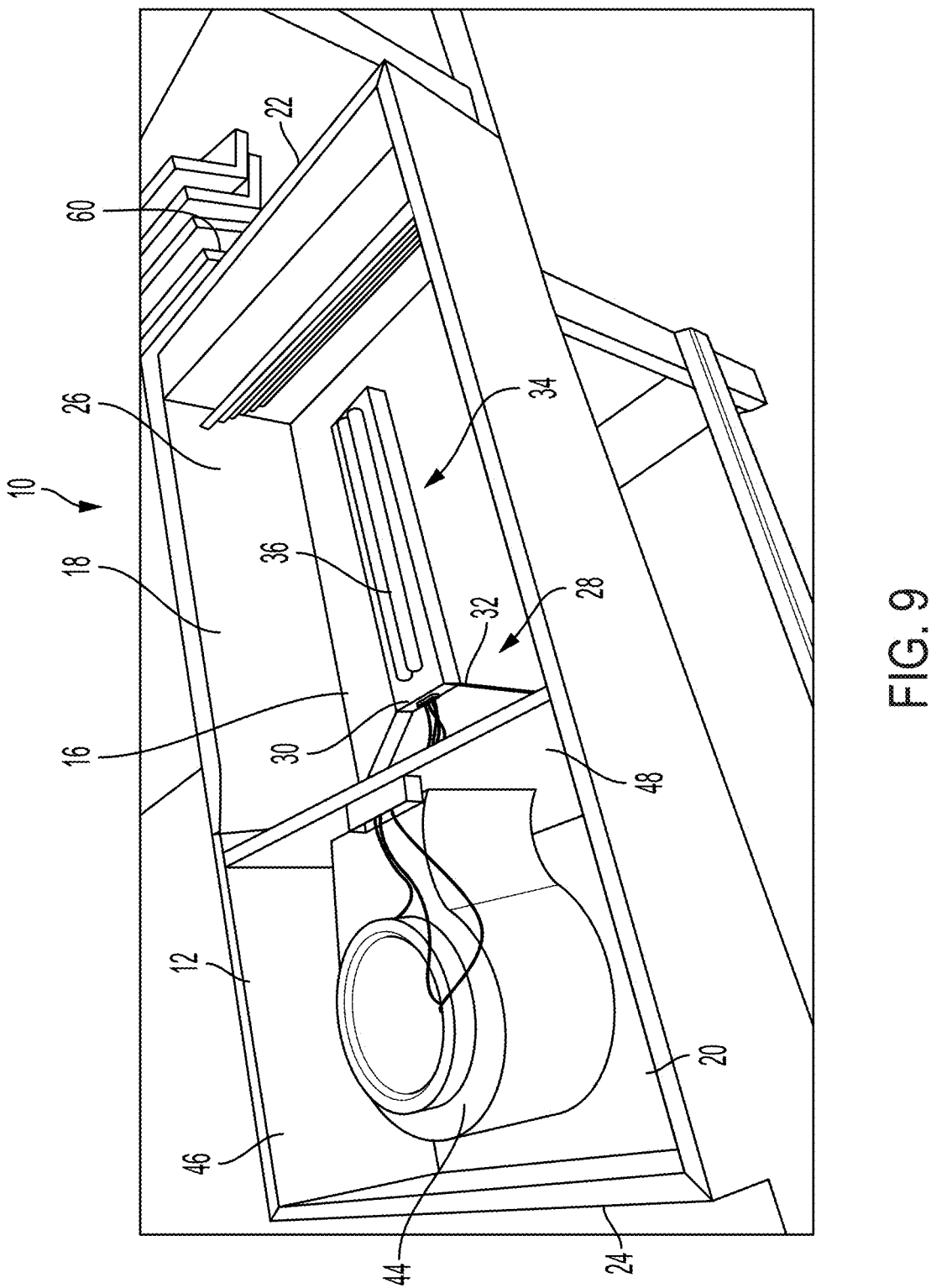
FIG. 9 is a view similar to FIG. 8, with the bottom main wall removed to show the internal components.

FIG. 7 shows basic electrical system for the purifier 10 in schematic form. Any system suitable for activating the fan 44 and bulb 36 may be used, and the illustrated design is not limiting. The non-limiting illustrated design includes the bulb 36, the fan 44, a power supply 100 for controlling electrical power to the fan 44, the UV ballast for controlling electrical power to the bulb 36, an interlock switch 102 (which may be activated by a manual switch on the purifier housing 12, by remote wired or wireless signals, or both), and the power supply 104 for delivering electrical power via the interlock switch 102. An indicator 106, such as an LED indicator on the exterior of the housing 12 (typically on the wall 14 or on the cover 15 so as to be visible), may also be included for informing the user when the UV bulb 36 is operating to emit UV radiation. The indicator 106 may also be used to indicate when the bulb 36 is inoperative, such as being broken, burnt out or otherwise not functioning, to inform the user that it needs replacement.

In the non-limiting illustrated embodiment, the air purifier 10 may have a volumetric turnover rate (the volume of air flowing through it per unit time) in the range of 50-159 cfm (cubic feet per minute), preferably 75-125 cfm, and even more preferably 90-100 cfm. The flow rate may be varied for other considerations, such as noise reduction, slower clean- ing (lower cfm) overnight to reduce energy consumption, higher cleaning when a work leaves the office when noise is not a concern, and the like. Because of the overall configu- ration of the design and the ability to manage UV radiation leakage with structure that helps with laminar flow, the volumetric turnover can be in those high ranges, while still providing adequate exposure of the airflow to the UV radiation for pathogenic efficacy.

Generally speaking, a model for evaluating the survival of pathogens subject to UV exposure may be the classical single stage decay model of the first order. The equation is:

$$S = e^{-kD}$$

where k is the UV rate constant in $m^2/J$ (for a target pathogen), D is the UV exposure dose in $J/m^2$, and S is the fractional survival of the pathogen. This model generally functions for disinfection rates on the order of 90-99%, and may be used to model the UV exposure dose. Because the UV exposure dose (D) is a function of the irradiance in $W/m^2$ multiplied by the exposure time, which in turn is related to the flow rate, the flow rate can be tailored depending on the pathogens anticipated, the irradiance of the bulb 36, the desired fractional survival rate, and other concerns such as energy consumption and the like. All these factors may be balanced depending on design needs.

Testing of UV emissions may be conducted in accordance with UL-507 testing protocol from Underwriters Laboratory. The standards in ANSI RP-27 for photobiological assess- ment may be used. The emission of UV-C radiation from the purifier, such as at either port 40, 52 is preferably less than 0.1 $\mu W/cm^2$ (which is not limiting). These references to existing standards refer to those in effect as of the present application's filing date. These are not binding or essential to the scope of the invention, as standards may change and compliance may vary between different jurisdictions.

Figure 13:
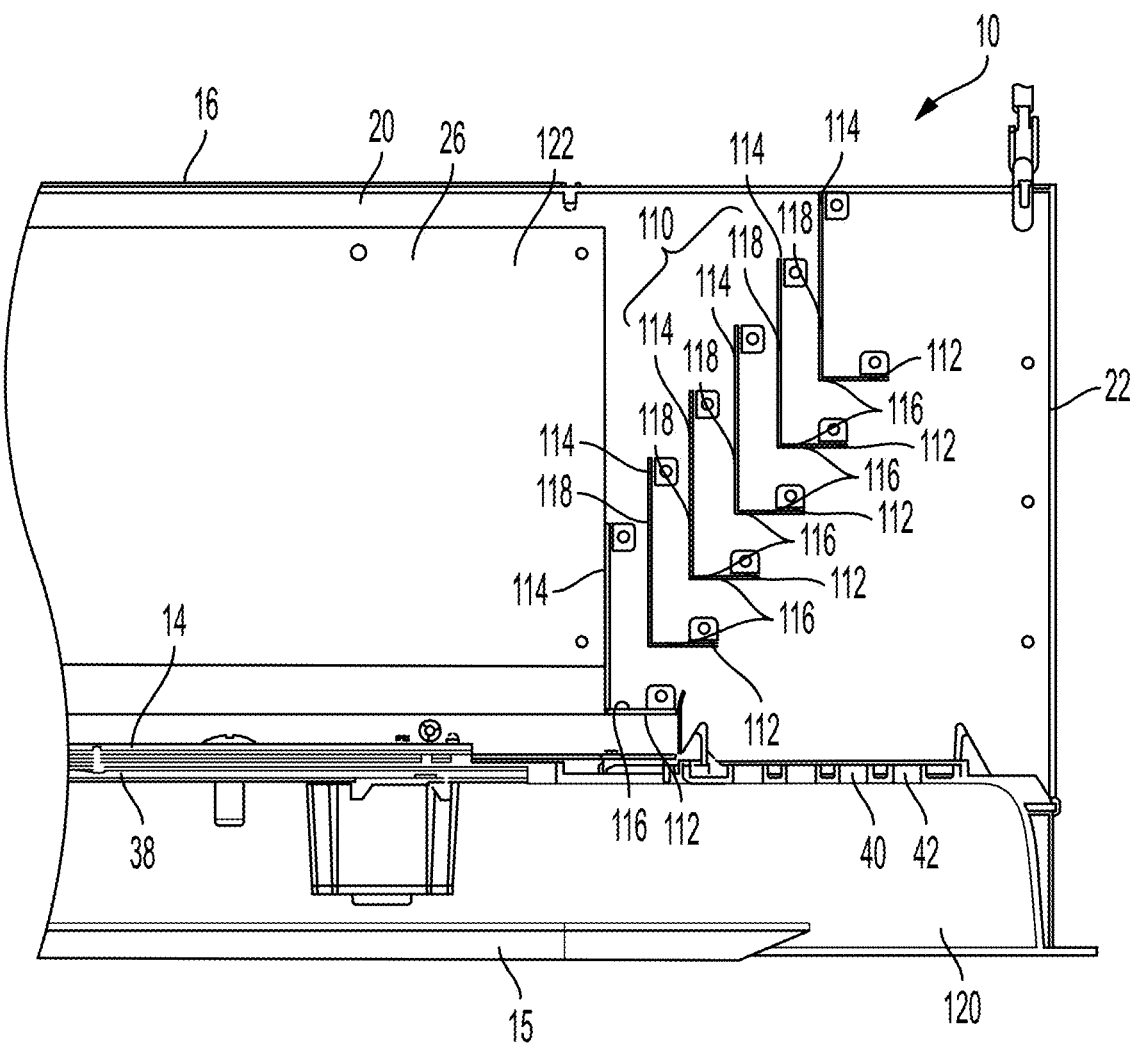
FIG. 13 is a view similar to FIG. 5 using further additional alternative baffles.

FIG. 13 illustrates another non-limiting arrangement for the baffles at the first or UV chamber end. The baffles 110 in FIG. 13 are the same as the baffles 60 in FIGS. 1-3 and 5-6, except they are arranged in an inverted manner. For conve- nience, the same reference numbers from those Figures will be used for common structures. The baffles 110 are similarly arranged in a nested, stepped and spaced apart configuration, with the diagonal direction of the stepped arrangement extending away from the first main wall 14 and away from the UV chamber 26, as was also the case in FIGS. 1-3 and 5. The embodiment of FIG. 13 may be used independently of or in conjunction with any of the baffle arrangements at the fan side/second end, such as those in the previous Figures or described above.

In the non-limiting embodiment of FIG. 13, the first baffle walls 112 (66 in the prior Figures) are oriented to extend towards the port 40 away from the second baffle walls 114

(68 in the prior Figures) and are located at the end of the second baffle walls 114 closer to the first main wall 14 and port 40. As illustrated, the plurality of baffles 110 are oriented such that the first baffle walls 112 extend towards the first port 40 essentially parallel to the first main wall 14 of the housing 12, but they may also be at an angle with respect to the first main wall 14 towards the port 40 (i.e., creating an obtuse angle to the second baffle walls 114 instead of the perpendicular angle illustrated). In the illus- trated embodiment, the second baffle walls 114 extend at an inner end of the first baffle walls 112 in a direction away from the first main wall 14, and as illustrated the second baffle walls 114 are essentially perpendicular to the first main wall 14 and the flow direction F. Thus, the first baffle walls 112 provide the series of port guiding surfaces 116 oriented towards the UV chamber port 40 for directing the air flowing between the sterilizing chamber 26 and the UV chamber port 40 in the direction of the UV chamber port 40, and specifically between the flow channels of the baffles 110 and the port 40. Likewise, the second baffle walls 114 provide the series of chamber guiding surfaces 118 for directing air flowing between the flow channels of the baffles 110 and the sterilizing chamber 26. As shown, the chamber guiding surfaces 118 direct the flow by collecting or receiv- ing the air flowing generally in the flow direction F, and directing it down towards the first baffle walls 112 for output to the port 40.

The inverted configuration in FIG. 13 provides reduced UV emissions due to the longer second walls 114, and particularly the one closest to the first main wall 14, facing the chamber 26.

Because the second wall 114 of the baffle 110 closest to the first main wall 14 has the entirety of its inner surface facing the chamber 26, that blocks a substantial amount of light from entering the baffle arrangement (and hence port 40). This differs from the design of FIG. 3 where some of the light impinging on the corresponding baffle 60 closest to the first main wall 14 may reflect into the plenum where the port 40 is located, thus allowing for some potential UV leakage. A trade off is that the baffle arrangement in FIG. 13 has some increase in turbulence. However, the inventor(s) has/have discovered the increase in turbulence is modest and does not materially affect the exposure of the air flow to UV radiation in the chamber 26 or the volumetric flow rate, while the UV emission is reduced in a substantial manner. Even though the walls 114 are perpendicular to the flow direction as illus- trated (which is not limiting), the baffles 110 still function to collect a large cross-section of air flow from the chamber 26. Either design can be used, and the choice may depend on overall size constraints, flow rates used, UV bulb luminance/ intensity, and the like.

The design of FIG. 13 can also be enhanced with the baffle surfaces having an anti-reflective characteristic as discussed above. For example, having the inner surfaces 118 (facing to the left in FIG. 13) of the second walls 114 that face in the direction of the light source 28 be anti-reflective, the radia- tion incident at an angle on those surfaces is not reflected (or its reflectance is significantly reduced), thus limiting the radiation directed to the UV chamber port 40. Additionally, having either or both surfaces 116 of each first wall 112 be anti-reflective as an additional option will likewise eliminate or reduce the radiation reflected off those surfaces toward the UV port 40 (including radiation that would reflect off them onto the inner surfaces of walls 114). Similarly, by having the outer surfaces 118 (facing to the right in FIG. 13) of walls 114 be anti-reflective, that can provide further reduc- tion of reflection towards the UV port 40. Although radiation from the bulb 30 is not directed at those outer surfaces, to the extent any amount of radiation is reflected thereon off a second wall 114 or the inner surface of a first wall 112, having those outer surfaces 118 of the baffles 110 be anti-reflective as a further option helps limit the amount of UV radiation leakage through the UV chamber port 40. As a further option, because the inner surface of the wall 114 on the baffle 110 closest to the first main wall 14 directly faces the chamber 26 and light reflected therefrom will not enter the baffle arrangement, that inner surface need not be anti-reflective, and may also be made reflective like the other surfaces discussed above bounding the chamber 26. That may increase the amount of radiation intensity within the chamber 26.

FIG. 13 also shows the cover 15, which is attached by a hinge and pivotable downwardly for access to the panel for changing the bulb 36, filters, or other maintenance/repair purposes. A plastic trim 120 is attached over the port 40, which helps direct the air through the port 40. A similar trim 121 may be used at the fan port 52 at the second end, or a single continuous trim can extend around the cover 15 to help direct the air flowing through the ports 40, 52. As also can be appreciated from FIG. 13, a reflective panel 122, as discussed above, is shown as being mounted to the inner surfaces of side walls 18, 20, and may also be on the inner surfaces of main walls 14, 16 as well.

As can be seen from the various Figures, the plurality of baffles used in the various embodiments at either the first or second end (the UV port end or the fan end) are arranged in a spaced apart arrangement to provide a series of flow channels including the port and chamber guiding surfaces. The use of multiple individual or separated channels is preferred for directing flow without substantial restriction, and the guiding surfaces direct the airflow therethrough with greater improvement because of the increased surface area the multiple baffles provide while maintaining a relatively large cross-sectional flow area. The use of a thin wall for the baffles, such as sheet metal, plastic in thin wall form, or the like, helps provide the increased surface area for airflow management while maintaining the larger cross-sectional flow area. For example, the walls may be in the range of 0.05-0.25 inches, and 10 gauge or 12 gauge stainless steel sheet metal (about 0.141 and 0.109 inches in thickness, respectively) are non-limiting examples. As can be seen, the baffles in each design may be arranged over essentially the entire height direction, thus allowing for larger cross-sectional areas for the air flow entering and exiting any given series of baffles. Likewise, the baffles may extend across the essentially the entire width direction, thus increasing the cross-sectional flow area even further.

The baffles at either end may have any configuration or design, and may be used in different combinations also (i.e. the baffles for the fan end in one embodiment may be used in a design with baffles at the UV port end from another embodiment). For example, instead of baffles with distinct angles between the walls defining the port and chamber guiding surfaces, curved baffles, including continuously curved ones, can be used, and it is understood that the portion of the curve adjacent the chamber 26 would be considered the chamber guiding surface and the portion adjacent a port would be considered the port guiding surface.

The foregoing detailed description has been provided to illustrate the structural and functional principles of the present invention and is not intended to be limiting. To the contrary, the present invention includes all modifications, substitutions, alterations, and equivalents within the spirit and scope of the following claims.

What is claimed:

1. An air purifier comprising:
   a housing for installation in or on a wall or ceiling of a building space;
   a UV light sterilizing chamber in the housing for directing a flow of air therethrough in a flow direction extending between first and second opposing ends of the chamber;
   a UV light source mounted in the sterilizing chamber for emitting UV light to sterilize air flowing through the sterilizing chamber, the UV light source being oriented in the flow direction so as to extend in the direction between the first and second ends;
   a first port on the housing communicated to the UV light sterilizing chamber at the first end thereof for permitting flow of the air between the sterilizing chamber and the building space via the first port, the first port being oriented at an angle to the flow direction for facing the building space;
   a fan for generating the flow of the air from the building space and through the UV light sterilizing chamber and first port, the fan being distal from the first port;
   a plurality of baffles mounted adjacent the first port,
   wherein the plurality of baffles are arranged in a spaced apart arrangement to provide a series of flow channels including a series of port guiding surfaces and a series of chamber guiding surfaces, the port guiding surfaces being configured to direct the air flowing between the flow channels and the first port and the chamber guiding surfaces being configured to direct the air flowing between the flow channels and the sterilizing chamber,
   wherein the port guiding surfaces are oriented towards the first port for directing the air flowing between the flow channels and the first port, and the chamber guiding surfaces for directing the air flowing between the flow channels and the sterilizing chamber are oriented generally perpendicularly to the flow direction.

2. The air purifier according to claim 1, wherein the baffles of the plurality thereof having anti-reflective surfaces that reduce or eliminate reflection of the UV light emitted by the UV light source to reduce or eliminate emittance through the first port.

3. The air purifier according to claim 1, wherein the plurality of baffles are arranged in a nested, spaced apart arrangement with the first baffle walls of adjacent baffles overlapping each other in a spaced apart manner and the second baffle walls overlapping each other in a spaced apart manner.

4. The air purifier according to claim 1, wherein the housing has first and second parallel main walls and side walls connecting the main walls, the first port being an opening in the first wall;
   wherein each baffle of the plurality thereof includes a first baffle wall extending towards the first port and a second baffle wall extending generally perpendicularly to the main walls at an inner end of the first baffle wall, the first baffle walls providing the port guiding surfaces and the second baffle walls providing the chamber guiding surfaces.

5. The air purifier according to claim 4, wherein each baffle of the plurality thereof has the first and second baffle walls thereof connected to one another.

6. The air purifier according to claim 5, wherein each baffle of the plurality thereof is L-shaped with the first and second baffle walls essentially perpendicular.

7. The air purifier according to claim 6, wherein the plurality of baffles are oriented such that the first baffle walls extend towards the first port essentially parallel to the first main wall of the housing and the second baffle walls are essentially perpendicular to the first main wall of the housing.

8. The air purifier according to claim 6, wherein the plurality of baffles are arranged in a stepped, nested, spaced apart arrangement with the first baffle walls of adjacent baffles overlapping each other in a spaced apart manner and the second baffle walls overlapping each other in a spaced apart manner.

9. The air purifier according to claim 7, wherein the plurality of baffles are arranged in a stepped, nested, spaced apart arrangement with the first baffle walls of adjacent baffles overlapping each other in a spaced apart manner and the second baffle walls overlapping each other in a spaced apart manner.

10. The air purifier according to claim 1, further comprising a second port on the housing communicated to the UV light sterilizing chamber at the second end thereof for permitting flow of the air between the sterilizing chamber and the building space via the second port, the second port being oriented at an angle to the flow direction for facing the building space;

wherein the plurality of baffles mounted adjacent the first port is a first plurality and the air purifier further comprises a second plurality of baffles mounted adjacent the second port, the fan being between the second plurality of baffles and the second port for generating flow via the second port, the baffles of the second plurality being arranged in a spaced apart arrangement to provide a series of flow channels including a series of port guiding surfaces and a series of chamber guiding surfaces, the port guiding surfaces being configured to direct the air flow between the flow channels and the fan generating the flow via the second port, the chamber guiding surfaces being oriented generally in the flow direction for directing the air flowing between the flow channels and the sterilizing chamber.

11. The air purifier according to claim 10, wherein the baffles of the second plurality thereof baffles have antireflective surfaces that reduces or eliminates reflection of the UV light emitted by the UV light source to reduce or eliminate emittance through the second port.

12. The air purifier according to claim 11, wherein the housing includes a fan chamber with a wall between the fan chamber and the sterilizing chamber, the wall having an opening for communicating the fan chamber and the sterilizing chamber, and wherein the fan chamber has the second port and the fan is positioned in the fan chamber.

13. The air purifier according to claim 12, wherein the fan is configured to draw the flow of air in from the building space through the second port and deliver the flow of air through the sterilizing chamber and out to the building space through the first port.

14. The air purifier according to claim 13, further comprising a filter mounted in the second port.

15. An air purifier comprising:

a housing having first and second main walls for installation in or on a wall or ceiling of a building space with the first main wall facing the building space;

a UV light sterilizing chamber in the housing for directing a flow of air therethrough in a flow direction extending between first and second opposing ends of the chamber;

a UV light source mounted in the sterilizing chamber for emitting UV light to sterilize air flowing through the sterilizing chamber, the UV light source being oriented in the flow direction so as to extend in the direction between the first and second ends;

a first port on the housing communicated to the UV light sterilizing chamber at the first end thereof for permitting flow of the air between the sterilizing chamber and the building space via the first port;

a second port on the housing communicated to the UV light sterilizing chamber at the second end thereof for permitting flow of the air between the sterilizing chamber and the building space via the second port;

a fan adjacent the second port for generating the flow of the air to draw the flow of air in from the building space through the second port and deliver the flow of air through the UV light sterilizing chamber and out the first port;

a plurality of baffles mounted adjacent the second port and the fan for receiving the air flowing out from the fan into the sterilizing chamber, the baffles of the plurality providing a series of port guiding surfaces for directing the air flowing from the fan generating the flow through the second port, the baffles of the plurality also providing a series of chamber guiding surfaces oriented generally in the flow direction for directing air flowing from the baffles into the sterilizing chamber;

wherein the plurality of baffles are arranged in a spaced apart arrangement to provide a series of flow channels including the port and chamber guiding surfaces with the port guiding surfaces extending away from the first main wall such that the flow channels open towards the second main wall;

wherein the spaced apart arrangement of the plurality of baffles is a stepped, nested, spaced apart arrangement that extends generally diagonally away from the fan and away from the first main wall.

16. The air purifier according to claim 15, wherein the port guiding surfaces are oriented generally perpendicularly to the flow direction.

17. The air purifier according to claim 15, wherein the the first and second main walls of the housing are parallel and the housing has side walls connecting the main walls, the first port being an opening in the first wall;

wherein each baffle of the plurality thereof includes a first baffle wall extending towards the sterilizing chamber and a second baffle wall extending generally perpendicularly to the main walls at an outer end of the first baffle wall, the first baffle walls providing the chamber guiding surfaces and the second baffle walls providing the port guiding surfaces.

18. The air purifier according to claim 17, wherein each baffle of the plurality thereof has the first and second baffle walls thereof connected to one another.

19. The air purifier according to claim 18, wherein each baffle of the plurality thereof is L-shaped with the first and second baffle walls essentially perpendicular.

20. The air purifier according to claim 19, wherein the plurality of baffles are oriented such that the first baffle walls are essentially parallel to the first main wall of the housing and the second baffle walls extend essentially perpendicular to the first main wall of the housing.

21. The air purifier according to claim 19, wherein the plurality of baffles are arranged in the stepped, nested, spaced apart arrangement with the first baffle walls of adjacent baffles overlapping each other in a spaced apart manner and the second baffle walls overlapping each other in a spaced apart manner.

22. The air purifier according to claim 20, wherein the plurality of baffles are arranged in the stepped, nested, spaced apart arrangement with the first baffle walls of adjacent baffles overlapping each other in a spaced apart manner and the second baffle walls overlapping each other in a spaced apart manner.

23. The air purifier according to claim 15, further comprising a cover on the first main wall that is removable or openable to the access the UV light source.

24. An air purifier comprising:

a housing for installation in or on a wall or ceiling of a building space;

a UV light sterilizing chamber in the housing for directing a flow of air therethrough in a flow direction extending between first and second opposing ends of the chamber;

a UV light source mounted in the sterilizing chamber for emitting UV light to sterilize air flowing through the sterilizing chamber;

a first port on the housing communicated to the UV light sterilizing chamber at the first end thereof for permitting flow of the air between the sterilizing chamber and the building space via the first port, the first port being oriented at an angle to the flow direction for facing the building space;

a fan for generating the flow of the air from the building space and through the UV light sterilizing chamber and first port, the fan being distal from the first port;

a plurality of baffles mounted adjacent the first port, wherein the plurality of baffles are arranged in a spaced apart arrangement to provide a series of flow channels including a series of port guiding surfaces and a series of chamber guiding surfaces, the port guiding surfaces being configured to direct the air flowing between the flow channels and the first port and the chamber guiding surfaces being configured to direct the air flowing between the flow channels and the sterilizing chamber, wherein the port guiding surfaces are oriented towards the first port for directing the air flowing between the flow channels and the first port, and the chamber guiding surfaces are oriented towards the sterilizing chamber generally in the flow direction for directing air flowing between the flow channels and the sterilizing chamber, wherein the housing has first and second main walls and side walls connecting the main walls, the first port being an opening in the first wall;

wherein each baffle of the plurality thereof includes a first baffle wall extending towards the sterilizing chamber and a second baffle wall extending toward the first port, the first baffle walls providing the chamber guiding surfaces and the second baffle walls providing the port guiding surfaces, wherein each baffle of the plurality thereof has the first and second baffle walls thereof connected to one another, wherein the plurality of baffles are oriented such that the first baffle walls extend essentially parallel to the first main wall and the flow direction and the second baffle walls extend at an angle toward the first main wall and the first port, wherein the plurality of baffles are arranged in a nested, spaced apart arrangement with the first baffle walls of adjacent baffles overlapping each other in a spaced apart manner and the second baffle walls overlapping each other in a spaced apart manner.

25. An air purifier comprising:

a housing for installation in or on a wall or ceiling of a building space;

a UV light sterilizing chamber in the housing for directing a flow of air therethrough in a flow direction extending between first and second opposing ends of the chamber;

a UV light source mounted in the sterilizing chamber for emitting UV light to sterilize air flowing through the sterilizing chamber;

a first port on the housing communicated to the UV light sterilizing chamber at the first end thereof for permitting flow of the air between the sterilizing chamber and the building space via the first port, the first port being oriented at an angle to the flow direction for facing the building space;

a fan for generating the flow of the air from the building space and through the UV light sterilizing chamber and first port, the fan being distal from the first port;

a plurality of baffles mounted adjacent the first port, wherein the plurality of baffles are arranged in a spaced apart arrangement to provide a series of flow channels including a series of port guiding surfaces and a series of chamber guiding surfaces, the port guiding surfaces being configured to direct the air flowing between the flow channels and the first port and the chamber guiding surfaces being configured to direct the air flowing between the flow channels and the sterilizing chamber, wherein the port guiding surfaces are oriented towards the first port for directing the air flowing between the flow channels and the first port, and the chamber guiding surfaces are oriented towards the sterilizing chamber generally in the flow direction for directing air flowing between the flow channels and the sterilizing chamber, wherein the housing has first and second main walls and side walls connecting the main walls, the first port being an opening in the first wall, wherein each baffle of the plurality thereof includes a first baffle wall extending towards the sterilizing chamber and a second baffle wall extending toward the first port, the first baffle walls providing the chamber guiding surfaces and the second baffle walls providing the port guiding surfaces, wherein each baffle of the plurality thereof has the first and second baffle walls thereof connected to one another, wherein the plurality of baffles are oriented such that the first baffle walls extend essentially parallel to the first main wall and the flow direction and the second baffle walls extend at an angle toward the first main wall and the first port, wherein the first and second baffle walls of each baffle of the plurality thereof are connected by at least one intermediate baffle wall.

26. An air purifier comprising:

a housing for installation in or on a wall or ceiling of a building space;

a UV light sterilizing chamber in the housing for directing a flow of air therethrough in a flow direction extending between first and second opposing ends of the chamber;

a UV light source mounted in the sterilizing chamber for emitting UV light to sterilize air flowing through the sterilizing chamber;

a first port on the housing communicated to the UV light sterilizing chamber at the first end thereof for permitting flow of the air between the sterilizing chamber and the building space via the first port, the first port being oriented at an angle to the flow direction for facing the building space;

a fan for generating the flow of the air from the building space and through the UV light sterilizing chamber and first port, the fan being distal from the first port;

a plurality of baffles mounted adjacent the first port, wherein the plurality of baffles are arranged in a spaced apart arrangement to provide a series of flow channels including a series of port guiding surfaces and a series of chamber guiding surfaces, the port guiding surfaces being configured to direct the air flowing between the flow channels and the first port and the chamber guiding surfaces being configured to direct the air flowing between the flow channels and the sterilizing chamber, the air purifier further comprising:

a second port on the housing communicated to the UV light sterilizing chamber at the second end thereof for permitting flow of the air between the sterilizing chamber and the building space via the second port, the second port being oriented at an angle to the flow direction for facing the building space;

wherein the plurality of baffles mounted adjacent the first port is a first plurality and the air purifier further comprises a second plurality of baffles mounted adjacent the second port, the fan being between the second plurality of baffles and the second port for generating flow via the second port, the baffles of the second plurality being arranged in a spaced apart arrangement to provide a series of flow channels including a series of port guiding surfaces and a series of chamber guiding surfaces, the port guiding surfaces being configured to direct the air flow between the flow channels and the fan generating the flow via the second port, the chamber guiding surfaces being oriented generally in the flow direction for directing the air flowing between the flow channels and the sterilizing chamber, wherein the housing includes a fan chamber with a wall between the fan chamber and the sterilizing chamber, the wall having an opening for communicating the fan chamber and the sterilizing chamber, and wherein the fan chamber has the second port and the fan is positioned in the fan chamber.

27. The air purifier according to claim 26, wherein the fan is configured to draw the flow of air in from the building space through the second port and deliver the flow of air through the sterilizing chamber and out to the building space through the first port.

28. The air purifier according to claim 27, further comprising a filter mounted in the second port.

29. An air purifier comprising:

a housing for installation in or on a wall or ceiling of a building space;

a UV light sterilizing chamber in the housing for directing a flow of air therethrough in a flow direction extending between first and second opposing ends of the chamber;

a UV light source mounted in the sterilizing chamber for emitting UV light to sterilize air flowing through the sterilizing chamber;

a first port on the housing communicated to the UV light sterilizing chamber at the first end thereof for permitting flow of the air between the sterilizing chamber and the building space via the first port;

a second port on the housing communicated to the UV light sterilizing chamber at the second end thereof for permitting flow of the air between the sterilizing chamber and the building space via the second port;

a fan adjacent the second port for generating the flow of the air to draw the flow of air in from the building space through the second port and deliver the flow of air through the UV light sterilizing chamber and out the first port;

a plurality of baffles mounted adjacent the second port and the fan for receiving the air flowing out from the fan into the sterilizing chamber, the baffles of the plurality providing a series of port guiding surfaces for directing the air flowing from the fan generating the flow through the second port, the baffles of the plurality also providing a series of chamber guiding surfaces oriented generally in the flow direction for directing air flowing from the baffles into the sterilizing chamber;

wherein the plurality of baffles are arranged in a spaced apart arrangement to provide a series of flow channels including the port and chamber guiding surface;

wherein the port guiding surfaces are oriented generally perpendicularly to the flow direction;

wherein the plurality of baffles are arranged in a stepped, nested, spaced apart arrangement.

30. The air purifier according to claim 29, wherein the stepped arrangement extends generally diagonally away from the fan and away from a first main wall including the second port.

31. The air purifier according to claim 15, wherein each baffle of the plurality thereof includes a first baffle wall providing the chamber guiding surfaces and a second baffle wall providing the port guiding surfaces, wherein the plurality of baffles are oriented such that the first baffle walls extend at a first angle towards the second main wall of the housing and the sterilizing chamber, and wherein the second baffle walls extend at a second angle toward the second main wall of the housing and the fan.

32. The air purifier according to claim 31, wherein the first and second walls of the baffles are connected in a V-shape.

33. An air purifier comprising:

a housing for installation in or on a wall or ceiling of a building space;

a UV light sterilizing chamber in the housing for directing a flow of air therethrough in a flow direction extending between first and second opposing ends of the chamber;

a UV light source mounted in the sterilizing chamber for emitting UV light to sterilize air flowing through the sterilizing chamber;

a first port on the housing communicated to the UV light sterilizing chamber at the first end thereof for permitting flow of the air between the sterilizing chamber and the building space via the first port, the first port being oriented at an angle to the flow direction for facing the building space;

a fan for generating the flow of the air from the building space and through the UV light sterilizing chamber and first port, the fan being distal from the first port;

a plurality of baffles mounted adjacent the first port, wherein the plurality of baffles are arranged in a spaced apart arrangement to provide a series of flow channels including a series of port guiding surfaces and a series of chamber guiding surfaces, the port guiding surfaces being configured to direct the air flowing between the flow channels and the first port and the chamber guiding surfaces being configured to direct the air flowing between the flow channels and the sterilizing chamber, wherein the port guiding surfaces are oriented towards the first port for directing the air flowing between the flow channels and the first port, and the chamber guiding surfaces are oriented towards the sterilizing chamber generally in the flow direction for directing air flowing between the flow channels and the sterilizing chamber, wherein the housing has first and second main walls and side walls connecting the main walls, the first port being an opening in the first wall;

wherein each baffle of the plurality thereof includes a first baffle wall extending towards the sterilizing chamber and a second baffle wall extending toward the first port, the first baffle walls providing the chamber guiding surfaces and the second baffle walls providing the port guiding surfaces, wherein each baffle of the plurality thereof has the first and second baffle walls thereof connected to one another, wherein the plurality of baffles are oriented such that the first baffle walls extend at a first angle towards the first main wall of the housing and the sterilizing chamber, and wherein the second baffle walls extend at a second angle toward the first main wall of the housing and the first port.

34. The air purifier according to claim 24, wherein each baffle of the plurality thereof is L-shaped with the first and second baffle walls essentially perpendicular.

35. The air purifier according to claim 25, wherein the plurality of baffles are arranged in a nested, spaced apart arrangement with the first baffle walls of adjacent baffles overlapping each other in a spaced apart manner, the second baffle walls overlapping each other in a spaced apart manner, and the intermediate baffle walls overlapping each other in a spaced apart manner.

36. The air purifier according to claim 25, wherein the at least one intermediate baffle wall includes a third baffle wall essentially parallel to the first baffle wall of the housing connected to the second baffle wall and a fourth baffle wall extending at an angle with respect to the flow direction towards the first main wall and connected to the first baffle wall and the third baffle wall.

37. The air purifier according to claim 33, wherein the plurality of baffles are arranged in a nested, spaced apart arrangement with the first baffle walls of adjacent baffles overlapping each other in a spaced apart manner and the second baffle walls overlapping each other in a spaced apart manner.

38. The air purifier according to claim 34, wherein the plurality of baffles are oriented such that the first baffle walls are essentially parallel to the first main wall of the housing and the second baffle walls extend towards the first port essentially perpendicular to the first main wall of the housing.

39. The air purifier according to claim 35, wherein the at least one intermediate baffle wall includes a third baffle wall essentially parallel to the first baffle wall of the housing connected to the second baffle wall and a fourth baffle wall extending at an angle with respect to the flow direction towards the first main wall and connected to the first baffle wall and the third baffle wall.

* * * * *